(12) United States Patent
Chen et al.

(10) Patent No.: US 12,145,974 B2
(45) Date of Patent: Nov. 19, 2024

(54) DUAL-TARGET FUSION PROTEINS COMPRISING FGF21 AND GLP-1, CONNECTED THROUGH A Fc PORTION OF AN IMMUNOGLOBULIN

(71) Applicant: SUNSHINE LAKE PHARMA CO., LTD., Guangdong (CN)

(72) Inventors: Chao Chen, Dongguan (CN); Shushan Lin, Dongguan (CN); Yu Li, Dongguan (CN); Xiaofeng Chen, Dongguan (CN); Liang Liu, Dongguan (CN); Zheng Fu, Dongguan (CN)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 1010 days.

(21) Appl. No.: 16/485,153

(22) PCT Filed: Mar. 14, 2018

(86) PCT No.: PCT/CN2018/078925
§ 371 (c)(1),
(2) Date: Aug. 10, 2019

(87) PCT Pub. No.: WO2018/166461
PCT Pub. Date: Sep. 20, 2018

(65) Prior Publication Data
US 2022/0127322 A1   Apr. 28, 2022

(30) Foreign Application Priority Data

Mar. 14, 2017   (CN) .......................... 201710148158.7
Feb. 8, 2018   (CN) .......................... 201810129427.X

(51) Int. Cl.
*A61K 38/18* (2006.01)
*A61P 3/04* (2006.01)
*C07K 14/50* (2006.01)
*C07K 14/605* (2006.01)

(52) U.S. Cl.
CPC .............. *C07K 14/605* (2013.01); *A61P 3/04* (2018.01); *C07K 14/50* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,452,966 B2 | 11/2008 | Glaesner et al. | |
| 7,491,697 B2 | 2/2009 | Beals et al. | |
| 7,576,190 B2 | 8/2009 | Glaesner et al. | |
| 7,582,607 B2 | 9/2009 | Frye et al. | |
| 8,034,770 B2 | 10/2011 | Belouski et al. | |
| 8,188,040 B2 | 5/2012 | Belouski et al. | |
| 8,273,854 B2 | 9/2012 | Glaesner et al. | |
| 8,361,963 B2 | 1/2013 | Belouski et al. | |
| 8,410,051 B2 | 4/2013 | Belouski et al. | |
| 8,541,369 B2 | 9/2013 | Dickinson et al. | |
| 8,557,769 B2 | 10/2013 | Coskun et al. | |
| 8,618,053 B2 | 12/2013 | Belouski et al. | |
| 8,642,546 B2 | 2/2014 | Belouski et al. | |
| 8,741,841 B2 | 6/2014 | Darling et al. | |
| 8,795,985 B2 | 8/2014 | Belouski et al. | |
| 8,835,385 B2 | 9/2014 | Belouski et al. | |
| 8,883,726 B2* | 11/2014 | Dickinson ................. A61P 3/10 530/399 |
| 8,927,492 B2 | 1/2015 | Darling et al. | |
| 9,006,400 B2 | 4/2015 | Boettcher et al. | |
| 9,266,935 B2 | 2/2016 | Boettcher et al. | |
| 9,273,106 B2 | 3/2016 | Belouski et al. | |
| 9,422,353 B2 | 8/2016 | Darling et al. | |
| 9,458,214 B2* | 10/2016 | Boettcher ................. A61P 3/00 |
| 9,493,530 B2* | 11/2016 | Belouski ................. C07K 14/50 |
| 10,011,642 B2 | 7/2018 | Belouski et al. | |
| 10,076,554 B2 | 9/2018 | Boettcher et al. | |
| 2009/0118190 A1 | 5/2009 | Beals et al. | |
| 2012/0035099 A1 | 2/2012 | Garibay et al. | |
| 2012/0172298 A1 | 7/2012 | Andersen et al. | |
| 2013/0203651 A1 | 8/2013 | Sommerfeld et al. | |
| 2013/0252884 A1 | 9/2013 | Garibay et al. | |
| 2014/0024586 A1 | 1/2014 | Coskun et al. | |
| 2014/0056893 A1 | 2/2014 | Coskun et al. | |
| 2014/0073563 A1* | 3/2014 | Boscheinen ............... A61P 9/10 514/6.9 |
| 2014/0142023 A1 | 5/2014 | Sommerfeld et al. | |

(Continued)

FOREIGN PATENT DOCUMENTS

WO   WO2008/145142   * 12/2008
WO      2016114633 A1    7/2016

(Continued)

OTHER PUBLICATIONS

Silva et al. J. Biol. Chem. 290(9): 5463-5469, 2015.*
Li et al. Int. J. Clin. Exp. Med. 8(3): 3607-3618, 2015.*
Glaesner et al. (Diabetes Metab. Res. Rev. 26: 287-296, 2010).*
Spiess et al. (J. Biol. Chem. 288(37): 26583-26593, 2013).*
Xu et al. (Cell. Immunol. 200: 16-26, 2000).*
Vidarsson et al. Frontiers in Immunol. 5(520): 1-17, 2014.*

(Continued)

*Primary Examiner* — Christine J Saoud

(74) *Attorney, Agent, or Firm* — Kam Wah Law

(57) ABSTRACT

Provided is a fusion protein containing GLP-1 and FGF21 linked through an immunoglobulin Fc portion. Each of the GLP-1 and FGF21 can be substituted with its analogues or variants and, the Fc portion, which can be derived from IgG4, can include substitutions that further enhance the fusion protein's stability and activity. These fragments can be linked together through peptide linkers. The fusion protein can be used clinically to reduce glucose and lipid levels and body weight.

18 Claims, 12 Drawing Sheets

Specification includes a Sequence Listing.

(56) References Cited

U.S. PATENT DOCUMENTS

| | | |
|---|---|---|
| 2014/0213512 A1 | 7/2014 | Ellison et al. |
| 2015/0231210 A1 | 8/2015 | Sommerfeld et al. |
| 2016/0194371 A1 | 7/2016 | Boscheinen et al. |
| 2018/0280474 A1 | 10/2018 | Xu et al. |

FOREIGN PATENT DOCUMENTS

| | | |
|---|---|---|
| WO | 2017074117 A1 | 5/2017 |
| WO | 2017074123 A1 | 5/2017 |
| WO | 2017093465 A1 | 6/2017 |

OTHER PUBLICATIONS

Murielle.M. Veniant et al.,Long-Acting FGF21 Has Enhanced Efficacy in Diet-Induced Obese Mice and in Obese Rhesus Monkeys,Endocrinology,Sep. 2012,153(9):4192-4203.

Randy Hecht et al.,Rationale-Based Engineering of a Potent Long-Acting FGF21 Analog for the Treatment of Type 2 Diabetes,PLOS ONE,Nov. 2012,vol. 7,Issue 11,e49345.

\* cited by examiner

SEQUENCE LISTING

<160> NUMBER OF SEQ ID NOS: 38

<210> SEQ ID NO 1
<211> LENGTH: 31
<212> TYPE: PRT
<213> ORGANISM: Artificial Sequence
<220> FEATURE:

<223> OTHER INFORMATION: Description of artificial sequence: synthetic
      protein

<400> SEQUENCE: 1

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 2
<211> LENGTH: 228
<212> TYPE: PRT
<213> ORGANISM: Artificial Sequence
<220> FEATURE:
<223> OTHER INFORMATION: Description of artificial sequence: synthetic
      protein

<400> SEQUENCE: 2

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly
225

<210> SEQ ID NO 3
<211> LENGTH: 275
<212> TYPE: PRT
<213> ORGANISM: Artificial Sequence
<220> FEATURE:
<223> OTHER INFORMATION: Description of artificial sequence: synthetic
      protein

<400> SEQUENCE: 3

His Gly Glu Gly Thr Phe Thr Ser Asp Val Ser Ser Tyr Leu Glu Glu

```
                1               5                  10                    15
       Gln Ala Ala Lys Glu Phe Ile Ala Trp Leu Val Lys Gly Gly Gly
                        20                 25                 30
       Gly Gly Gly Ser Gly Gly Gly Ser Gly Gly Gly Ser Ala Glu
                        35                 40                 45
       Ser Lys Tyr Gly Pro Pro Cys Pro Pro Cys Pro Ala Pro Glu Ala Ala
                        50                 55                 60
       Gly Gly Pro Ser Val Phe Leu Phe Pro Pro Lys Pro Lys Asp Thr Leu
       65                       70                 75                 80
       Met Ile Ser Arg Thr Pro Glu Val Thr Cys Val Val Val Asp Val Ser
                        85                 90                 95
       Gln Glu Asp Pro Glu Val Gln Phe Asn Trp Tyr Val Asp Gly Val Glu
                        100                105                110
       Val His Asn Ala Lys Thr Lys Pro Arg Glu Glu Gln Phe Asn Ser Thr
                        115                120                125
       Tyr Arg Val Val Ser Val Leu Thr Val Leu His Gln Asp Trp Leu Asn
                        130                135                140
       Gly Lys Glu Tyr Lys Cys Lys Val Ser Asn Lys Gly Leu Pro Ser Ser
       145                      150                155                160
       Ile Glu Lys Thr Ile Ser Lys Ala Lys Gly Gln Pro Arg Glu Pro Gln
                        165                170                175
       Val Tyr Thr Leu Pro Pro Ser Gln Glu Glu Met Thr Lys Asn Gln Val
                        180                185                190
       Ser Leu Thr Cys Leu Val Lys Gly Phe Tyr Pro Ser Asp Ile Ala Val
                        195                200                205
       Glu Trp Glu Ser Asn Gly Gln Pro Glu Asn Asn Tyr Lys Thr Thr Pro
                        210                215                220
       Pro Val Leu Asp Ser Asp Gly Ser Phe Phe Leu Tyr Ser Arg Leu Thr
       225                      230                235                240
       Val Asp Lys Ser Arg Trp Gln Glu Gly Asn Val Phe Ser Cys Ser Val
                        245                250                255
       Met His Glu Ala Leu His Asn His Tyr Thr Gln Lys Ser Leu Ser Leu
                        260                265                270
       Ser Leu Gly
                275

<210> SEQ ID NO 4
<211> LENGTH: 424
<212> TYPE: PRT
<213> ORGANISM: Artificial Sequence
<220> FEATURE:
<223> OTHER INFORMATION: Description of artificial sequence: synthetic
      protein

<400> SEQUENCE: 4

Glu Ser Lys Tyr Gly Pro Pro Cys Pro Pro Cys Pro Ala Pro Glu Ala
       1                5                 10                 15
       Ala Gly Gly Pro Ser Val Phe Leu Phe Pro Pro Lys Pro Lys Asp Thr
                        20                 25                 30
       Leu Met Ile Ser Arg Thr Pro Glu Val Thr Cys Val Val Val Asp Val
                        35                 40                 45
       Ser Gln Glu Asp Pro Glu Val Gln Phe Asn Trp Tyr Val Asp Gly Val
                        50                 55                 60
       Glu Val His Asn Ala Lys Thr Lys Pro Arg Glu Glu Gln Phe Asn Ser
       65                       70                 75                 80
```

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Gly Gly Gly Ser Gly Gly Gly Ser Gly Gly Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu Ser Met Val Gly Gly Ser Gln
                405                 410                 415

Gly Arg Ser Pro Ser Tyr Ala Ser
                420

<210> SEQ ID NO 5
<211> LENGTH: 470
<212> TYPE: PRT
<213> ORGANISM: Artificial Sequence
<220> FEATURE:
<223> OTHER INFORMATION: Description of artificial sequence: synthetic
      protein

<400> SEQUENCE: 5

His Gly Glu Gly Thr Phe Thr Ser Asp Val Ser Ser Tyr Leu Glu Glu
1               5                   10                  15
```

```
Gln Ala Ala Lys Glu Phe Ile Ala Trp Leu Val Lys Gly Gly Gly
             20                  25                  30
Gly Gly Gly Ser Gly Gly Gly Ser Gly Gly Gly Ser Glu Ser
         35                  40                  45
Lys Tyr Gly Pro Pro Cys Pro Pro Cys Pro Ala Pro Glu Ala Ala Gly
 50                  55                  60
Gly Pro Ser Val Phe Leu Phe Pro Pro Lys Pro Lys Asp Thr Leu Met
 65                  70                  75                  80
Ile Ser Arg Thr Pro Glu Val Thr Cys Val Val Val Asp Val Ser Gln
                 85                  90                  95
Glu Asp Pro Glu Val Gln Phe Asn Trp Tyr Val Asp Gly Val Glu Val
                100                 105                 110
His Asn Ala Lys Thr Lys Pro Arg Glu Glu Gln Phe Asn Ser Thr Tyr
            115                 120                 125
Arg Val Val Ser Val Leu Thr Val Leu His Gln Asp Trp Leu Asn Gly
    130                 135                 140
Lys Glu Tyr Lys Cys Lys Val Ser Asn Lys Gly Leu Pro Ser Ser Ile
145                 150                 155                 160
Glu Lys Thr Ile Ser Lys Ala Lys Gly Gln Pro Arg Glu Pro Gln Val
                165                 170                 175
Tyr Thr Leu Pro Pro Ser Gln Glu Met Thr Lys Asn Gln Val Ser
            180                 185                 190
Leu Thr Cys Leu Val Lys Gly Phe Tyr Pro Ser Asp Ile Ala Val Glu
    195                 200                 205
Trp Glu Ser Asn Gly Gln Pro Glu Asn Asn Tyr Lys Thr Thr Pro Pro
    210                 215                 220
Val Leu Asp Ser Asp Gly Ser Phe Phe Leu Tyr Ser Lys Leu Thr Val
225                 230                 235                 240
Asp Lys Ser Arg Trp Gln Glu Gly Asn Val Phe Ser Cys Ser Val Met
                245                 250                 255
His Glu Ala Leu His Asn His Tyr Thr Gln Lys Ser Leu Ser Leu Ser
            260                 265                 270
Leu Gly Gly Gly Gly Ser Gly Gly Gly Ser Gly Gly Gly Gly
    275                 280                 285
Ser His Pro Ile Pro Asp Ser Ser Pro Leu Leu Gln Phe Gly Gly Gln
    290                 295                 300
Val Arg Gln Arg Tyr Leu Tyr Thr Asp Asp Ala Gln Gln Thr Glu Ala
305                 310                 315                 320
His Leu Glu Ile Arg Glu Asp Gly Thr Val Gly Gly Ala Ala Asp Gln
                325                 330                 335
Ser Pro Glu Ser Leu Leu Gln Leu Lys Ala Leu Lys Pro Gly Val Ile
            340                 345                 350
Gln Ile Leu Gly Val Lys Thr Ser Arg Phe Leu Cys Gln Arg Pro Asp
    355                 360                 365
Gly Ala Leu Tyr Gly Ser Leu His Phe Asp Pro Glu Ala Cys Ser Phe
    370                 375                 380
Arg Glu Arg Leu Leu Glu Asp Gly Tyr Asn Val Tyr Gln Ser Glu Ala
385                 390                 395                 400
His Gly Leu Pro Leu His Leu Pro Gly Asn Lys Ser Pro His Arg Asp
                405                 410                 415
Pro Ala Pro Arg Gly Pro Ala Arg Phe Leu Pro Leu Pro Gly Leu Pro
            420                 425                 430
```

```
Pro Ala Leu Pro Glu Pro Pro Gly Ile Leu Ala Pro Gln Pro Pro Asp
            435                 440                 445

Val Gly Ser Ser Asp Pro Leu Ser Met Val Gly Gly Ser Gln Gly Arg
    450                 455                 460

Ser Pro Ser Tyr Ala Ser
465                 470

<210> SEQ ID NO 6
<211> LENGTH: 181
<212> TYPE: PRT
<213> ORGANISM: Artificial Sequence
<220> FEATURE:
<223> OTHER INFORMATION: Description of artificial sequence: synthetic
      protein

<400> SEQUENCE: 6

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser
                165                 170                 175

Pro Ser Tyr Ala Ser
            180

<210> SEQ ID NO 7
<211> LENGTH: 31
<212> TYPE: PRT
<213> ORGANISM: Artificial Sequence
<220> FEATURE:
<223> OTHER INFORMATION: Description of artificial sequence: synthetic
      protein
<220> FEATURE:
<221> NAME/KEY: misc_feature
<222> LOCATION: (2)..(2)
<223> OTHER INFORMATION: Xaa at position 2 is Gly or Val
<220> FEATURE:
<221> NAME/KEY: misc_feature
<222> LOCATION: (16)..(16)
<223> OTHER INFORMATION: Xaa at position 16 is Glu or Gly
<220> FEATURE:
<221> NAME/KEY: misc_feature
<222> LOCATION: (27)..(28)
<223> OTHER INFORMATION: Xaa at position 27 is Val or Lys. Xaa at
      position 28 is Lys or Asn
<220> FEATURE:
<221> NAME/KEY: misc_feature
```

```
<222> LOCATION: (30)..(31)
<223> OTHER INFORMATION: Xaa at position 30 is Gly or Glu. Xaa at
      position 31 is Gly or Pro

<400> SEQUENCE: 7

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Xaa Xaa Gly Xaa Xaa
            20                  25                  30

<210> SEQ ID NO 8
<211> LENGTH: 229
<212> TYPE: PRT
<213> ORGANISM: Artificial Sequence
<220> FEATURE:
<223> OTHER INFORMATION: Description of artificial sequence: synthetic
      protein
<220> FEATURE:
<221> NAME/KEY: misc_feature
<222> LOCATION: (15)..(17)
<223> OTHER INFORMATION: Xaa at position 15 is Pro or Glu. Xaa at
      position 16 is Phe, Val or Ala. Xaa at position 17 is Leu, Glu or
      Ala
<220> FEATURE:
<221> NAME/KEY: misc_feature
<222> LOCATION: (79)..(79)
<223> OTHER INFORMATION: Xaa at position 79 is Asn or Ala
<220> FEATURE:
<221> NAME/KEY: misc_feature
<222> LOCATION: (229)..(229)
<223> OTHER INFORMATION: Xaa at position 229 is Lys or absent

<400> SEQUENCE: 8

Glu Ser Lys Tyr Gly Pro Pro Cys Pro Pro Cys Pro Ala Pro Xaa Xaa
1               5                   10                  15

Xaa Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Xaa Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220
```

Leu Ser Leu Gly Xaa
225

<210> SEQ ID NO 9
<211> LENGTH: 181
<212> TYPE: PRT
<213> ORGANISM: Artificial Sequence
<220> FEATURE:
<223> OTHER INFORMATION: Description of artificial sequence: synthetic
      protein
<220> FEATURE:
<221> NAME/KEY: misc_feature
<222> LOCATION: (45)..(45)
<223> OTHER INFORMATION: Xaa at position 45 is selected from Ala, Lys,
      Arg, Glu or Gln
<220> FEATURE:
<221> NAME/KEY: misc_feature
<222> LOCATION: (98)..(98)
<223> OTHER INFORMATION: Xaa at position 98 is selected from Leu, Asp,
      Arg, Glu, Gln, Lys or Thr
<220> FEATURE:
<221> NAME/KEY: misc_feature
<222> LOCATION: (100)..(100)
<223> OTHER INFORMATION: Xaa at position 100 is selected from Leu or Lys
<220> FEATURE:
<221> NAME/KEY: misc_feature
<222> LOCATION: (118)..(118)
<223> OTHER INFORMATION: Xaa at position 118 is selected from Leu or Cys
<220> FEATURE:
<221> NAME/KEY: misc_feature
<222> LOCATION: (134)..(134)
<223> OTHER INFORMATION: Xaa at position 134 is selected from Ala or Cys
<220> FEATURE:
<221> NAME/KEY: misc_feature
<222> LOCATION: (150)..(152)
<223> OTHER INFORMATION: Xaa at position 150 is selected from Pro or
      Ala. Xaa at position 151 is selected from Gly or Ala. Xaa at
      position 152 is selected from Ile or Val
<220> FEATURE:
<221> NAME/KEY: misc_feature
<222> LOCATION: (167)..(167)
<223> OTHER INFORMATION: Xaa at position 167 is selected from Ser, His,
      Cys or Arg
<220> FEATURE:
<221> NAME/KEY: misc_feature
<222> LOCATION: (170)..(172)
<223> OTHER INFORMATION: Xaa at position 170 is selected from Gly, Glu,
      Ala, Asp or Ser at position 170. Xaa at position 171 is selected
      from Pro, Ala, Glu, Gln, Trp, Cys, Gly or Thr; Xaa at position 172
      is selected from Ser, Leu, Val or Met
<220> FEATURE:
<221> NAME/KEY: misc_feature
<222> LOCATION: (175)..(175)
<223> OTHER INFORMATION: Xaa at position 175 is selected from Arg, Leu,
      His or Pro
<220> FEATURE:
<221> NAME/KEY: misc_feature
<222> LOCATION: (179)..(180)
<223> OTHER INFORMATION: Xaa at position 179 is selected from Tyr, Ser,
      Ala or Phe. Xaa at position 180 is selected from Ala, Ser, Glu or
      Gly

<400> SEQUENCE: 9

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Xaa Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

```
Ala Leu Tyr Gly Ser Leu His Phe Asp Pro Glu Ala Cys Ser Phe Arg
                85                  90                  95

Glu Xaa Leu Xaa Glu Asp Gly Tyr Asn Val Tyr Gln Ser Glu Ala His
            100                 105                 110

Gly Leu Pro Leu His Xaa Pro Gly Asn Lys Ser Pro His Arg Asp Pro
        115                 120                 125

Ala Pro Arg Gly Pro Xaa Arg Phe Leu Pro Leu Pro Gly Leu Pro Pro
    130                 135                 140

Ala Leu Pro Glu Pro Xaa Xaa Xaa Leu Ala Pro Gln Pro Pro Asp Val
145                 150                 155                 160

Gly Ser Ser Asp Pro Leu Xaa Met Val Xaa Xaa Xaa Gln Gly Xaa Ser
                165                 170                 175

Pro Ser Xaa Xaa Ser
            180

<210> SEQ ID NO 10
<211> LENGTH: 31
<212> TYPE: PRT
<213> ORGANISM: Artificial Sequence
<220> FEATURE:
<223> OTHER INFORMATION: Description of artificial sequence: synthetic
      protein
<220> FEATURE:
<221> NAME/KEY: misc_feature
<222> LOCATION: (2)..(2)
<223> OTHER INFORMATION: Xaa at position 2 is Gly or Val
<220> FEATURE:
<221> NAME/KEY: misc_feature
<222> LOCATION: (16)..(16)
<223> OTHER INFORMATION: Xaa at position 16 is Glu or Gly
<220> FEATURE:
<221> NAME/KEY: misc_feature
<222> LOCATION: (30)..(30)
<223> OTHER INFORMATION: Xaa at position 30 is Gly or GIu

<400> SEQUENCE: 10

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Xaa Gly
            20                  25                  30

<210> SEQ ID NO 11
<211> LENGTH: 229
<212> TYPE: PRT
<213> ORGANISM: Artificial Sequence
<220> FEATURE:
<223> OTHER INFORMATION: Description of artificial sequence: synthetic
      protein
<220> FEATURE:
<221> NAME/KEY: misc_feature
<222> LOCATION: (16)..(17)
<223> OTHER INFORMATION: Xaa at position 16 is Phe, Val or Ala. Xaa at
      position 17 is Leu, Glu or Ala
<220> FEATURE:
<221> NAME/KEY: misc_feature
<222> LOCATION: (229)..(229)
<223> OTHER INFORMATION: Xaa at position 229 is Lys or absent

<400> SEQUENCE: 11

Glu Ser Lys Tyr Gly Pro Pro Cys Pro Pro Cys Pro Ala Pro Glu Xaa
1               5                   10                  15

Xaa Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45
```

```
Ser Gln Glu Asp Pro Glu Val Gln Phe Asn Trp Tyr Val Asp Gly Val
 50                  55                  60
Glu Val His Asn Ala Lys Thr Lys Pro Arg Glu Glu Gln Phe Asn Ser
 65                  70                  75                  80
Thr Tyr Arg Val Val Ser Val Leu Thr Val Leu His Gln Asp Trp Leu
                 85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
        115                 120                 125
Gln Val Tyr Thr Leu Pro Pro Ser Gln Glu Glu Met Thr Lys Asn Gln
130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Lys Leu
            180                 185                 190
Thr Val Asp Lys Ser Arg Trp Gln Gln Gly Asn Val Phe Ser Cys Ser
        195                 200                 205
Val Met His Glu Ala Leu His Asn His Tyr Thr Gln Lys Ser Leu Ser
210                 215                 220
Leu Ser Leu Gly Xaa
225

<210> SEQ ID NO 12
<211> LENGTH: 181
<212> TYPE: PRT
<213> ORGANISM: Artificial Sequence
<220> FEATURE:
<223> OTHER INFORMATION: Description of artificial sequence: synthetic
      protein
<220> FEATURE:
<221> NAME/KEY: misc_feature
<222> LOCATION: (98)..(98)
<223> OTHER INFORMATION: Xaa at position 98 is selected from Leu, Asp,
      Arg or Glu
<220> FEATURE:
<221> NAME/KEY: misc_feature
<222> LOCATION: (167)..(167)
<223> OTHER INFORMATION: Xaa at position 167 is selected from Ser, His,
      Cys or Arg
<220> FEATURE:
<221> NAME/KEY: misc_feature
<222> LOCATION: (171)..(171)
<223> OTHER INFORMATION: Xaa at position 171 is selected from Ala or Gly
<220> FEATURE:
<221> NAME/KEY: misc_feature
<222> LOCATION: (175)..(175)
<223> OTHER INFORMATION: Xaa at position 175 is selected from Arg, Leu,
      or Pro
<220> FEATURE:
<221> NAME/KEY: misc_feature
<222> LOCATION: (179)..(179)
<223> OTHER INFORMATION: The Xaa at position 179 is selected from Tyr,
      Ser or Phe

<400> SEQUENCE: 12

His Pro Ile Pro Asp Ser Ser Pro Leu Leu Gln Phe Gly Gly Gln Val
 1               5                  10                  15
Arg Gln Arg Tyr Leu Tyr Thr Asp Asp Ala Gln Gln Thr Glu Ala His
                 20                  25                  30
Leu Glu Ile Arg Glu Asp Gly Thr Val Gly Gly Ala Val Asp Gln Ser
```

```
                35                  40                  45

Pro Glu Ser Leu Leu Gln Leu Lys Ala Leu Lys Pro Gly Val Ile Gln
            50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Xaa Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Xaa Met Val Gly Xaa Ser Gln Gly Xaa Ser
                165                 170                 175

Pro Ser Xaa Ala Ser
            180

<210> SEQ ID NO 13
<211> LENGTH: 15
<212> TYPE: PRT
<213> ORGANISM: Artificial Sequence
<220> FEATURE:
<223> OTHER INFORMATION: Description of artificial sequence: synthetic
      protein

<400> SEQUENCE: 13

Gly Gly Gly Gly Ser Gly Gly Gly Gly Ser Gly Gly Gly Gly Ser
 1               5                  10                  15

<210> SEQ ID NO 14
<211> LENGTH: 31
<212> TYPE: PRT
<213> ORGANISM: Artificial Sequence
<220> FEATURE:
<223> OTHER INFORMATION: Description of artificial sequence: synthetic
      protein

<400> SEQUENCE: 14

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
                20                  25                  30

<210> SEQ ID NO 15
<211> LENGTH: 181
<212> TYPE: PRT
<213> ORGANISM: Artificial Sequence
<220> FEATURE:
<223> OTHER INFORMATION: Description of artificial sequence: synthetic
      protein

<400> SEQUENCE: 15

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45
```

```
Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 16
<211> LENGTH: 470
<212> TYPE: PRT
<213> ORGANISM: Artificial Sequence
<220> FEATURE:
<223> OTHER INFORMATION: Description of artificial sequence: synthetic
      protein

<400> SEQUENCE: 16

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Glu Ser
            35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
            100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
            130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
            195                 200                 205

Trp Glu Ser Asn Gly Gln Pro Glu Asn Asn Tyr Lys Thr Thr Pro Pro
```

```
                    210                 215                 220
Val Leu Asp Ser Asp Gly Ser Phe Phe Leu Tyr Ser Arg Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
                260                 265                 270

Leu Gly Gly Gly Gly Ser Gly Gly Gly Ser Gly Gly Gly Gly
                275                 280                 285

Ser His Pro Ile Pro Asp Ser Ser Pro Leu Leu Gln Phe Gly Gly Gln
                290                 295                 300

Val Arg Gln Arg Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
                340                 345                 350

Gln Ile Leu Gly Val Lys Thr Ser Arg Phe Leu Cys Gln Arg Pro Asp
                355                 360                 365

Gly Ala Leu Tyr Gly Ser Leu His Phe Asp Pro Glu Ala Cys Ser Phe
370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
                420                 425                 430

Pro Ala Leu Pro Glu Pro Pro Gly Ile Leu Ala Pro Gln Pro Pro Asp
                435                 440                 445

Val Gly Ser Ser Asp Pro Leu Ser Met Val Gly Gly Ser Gln Gly Arg
                450                 455                 460

Ser Pro Ser Tyr Ala Ser
465                 470

<210> SEQ ID NO 17
<211> LENGTH: 470
<212> TYPE: PRT
<213> ORGANISM: Artificial Sequence
<220> FEATURE:
<223> OTHER INFORMATION: Description of artificial sequence: synthetic
      protein

<400> SEQUENCE: 17

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Glu Ser
                35                  40                  45

Lys Tyr Gly Pro Pro Cys Pro Pro Cys Pro Ala Pro Glu Ala Ala Gly
50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95
```

```
Glu Asp Pro Glu Val Gln Phe Asn Trp Tyr Val Asp Gly Val Glu Val
            100                 105                 110

His Asn Ala Lys Thr Lys Pro Arg Glu Glu Gln Phe Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Gly Gly Gly Ser Gly Gly Gly Ser Gly Gly Gly Gly
        275                 280                 285

Ser His Pro Ile Pro Asp Ser Ser Pro Leu Leu Gln Phe Gly Gly Gln
    290                 295                 300

Val Arg Gln Arg Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
            340                 345                 350

Gln Ile Leu Gly Val Lys Thr Ser Arg Phe Leu Cys Gln Arg Pro Asp
        355                 360                 365

Gly Ala Leu Tyr Gly Ser Leu His Phe Asp Pro Glu Ala Cys Ser Phe
    370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
            420                 425                 430

Pro Ala Leu Pro Glu Pro Pro Gly Ile Leu Ala Pro Gln Pro Pro Asp
        435                 440                 445

Val Gly Ser Ser Asp Pro Leu Ser Met Val Gly Gly Ser Gln Gly Arg
    450                 455                 460

Ser Pro Ser Phe Ala Ser
465                 470

<210> SEQ ID NO 18
<211> LENGTH: 470
<212> TYPE: PRT
<213> ORGANISM: Artificial Sequence
<220> FEATURE:
<223> OTHER INFORMATION: Description of artificial sequence: synthetic
```

```
    protein

<400> SEQUENCE: 18

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Glu Ser
        35                  40                  45

Lys Tyr Gly Pro Pro Cys Pro Pro Cys Pro Ala Pro Glu Ala Ala Gly
        50              55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
            100                 105                 110

His Asn Ala Lys Thr Lys Pro Arg Glu Glu Gln Phe Asn Ser Thr Tyr
        115                 120                 125

Arg Val Val Ser Val Leu Thr Val Leu His Gln Asp Trp Leu Asn Gly
130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Gly Gly Gly Ser Gly Gly Gly Ser Gly Gly Gly Gly
        275                 280                 285

Ser His Pro Ile Pro Asp Ser Ser Pro Leu Leu Gln Phe Gly Gly Gln
    290                 295                 300

Val Arg Gln Arg Tyr Leu Tyr Thr Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
            340                 345                 350

Gln Ile Leu Gly Val Lys Thr Ser Arg Phe Leu Cys Gln Arg Pro Asp
        355                 360                 365

Gly Ala Leu Tyr Gly Ser Leu His Phe Asp Pro Glu Ala Cys Ser Phe
    370                 375                 380

Arg Glu Arg Leu Leu Glu Asp Gly Tyr Asn Val Tyr Gln Ser Glu Ala
385                 390                 395                 400
```

```
His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
                420                 425                 430

Pro Ala Leu Pro Glu Pro Pro Gly Ile Leu Ala Pro Gln Pro Pro Asp
                435                 440                 445

Val Gly Ser Ser Asp Pro Leu Ser Met Val Gly Ala Ser Gln Gly Arg
450                 455                 460

Ser Pro Ser Tyr Ala Ser
465                 470

<210> SEQ ID NO 19
<211> LENGTH: 470
<212> TYPE: PRT
<213> ORGANISM: Artificial Sequence
<220> FEATURE:
<223> OTHER INFORMATION: Description of artificial sequence: synthetic
      protein

<400> SEQUENCE: 19

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Ser Glu Ser
                35                  40                  45

Lys Tyr Gly Pro Pro Cys Pro Pro Cys Pro Ala Pro Glu Ala Ala Gly
        50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
            130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
                180                 185                 190

Leu Thr Cys Leu Val Lys Gly Phe Tyr Pro Ser Asp Ile Ala Val Glu
            195                 200                 205

Trp Glu Ser Asn Gly Gln Pro Glu Asn Asn Tyr Lys Thr Thr Pro Pro
            210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
                260                 265                 270

Leu Gly Gly Gly Gly Ser Gly Gly Gly Ser Gly Gly Gly
            275                 280                 285
```

-continued

```
Ser His Pro Ile Pro Asp Ser Ser Pro Leu Leu Gln Phe Gly Gly Gln
    290                 295                 300

Val Arg Gln Arg Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
            340                 345                 350

Gln Ile Leu Gly Val Lys Thr Ser Arg Phe Leu Cys Gln Arg Pro Asp
        355                 360                 365

Gly Ala Leu Tyr Gly Ser Leu His Phe Asp Pro Glu Ala Cys Ser Phe
    370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
            420                 425                 430

Pro Ala Leu Pro Glu Pro Gly Ile Leu Ala Pro Gln Pro Pro Asp
        435                 440                 445

Val Gly Ser Ser Asp Pro Leu His Met Val Gly Ala Ser Gln Gly Arg
    450                 455                 460

Ser Pro Ser Tyr Ala Ser
465                 470
```

<210> SEQ ID NO 20
<211> LENGTH: 470
<212> TYPE: PRT
<213> ORGANISM: Artificial Sequence
<220> FEATURE:
<223> OTHER INFORMATION: Description of artificial sequence: synthetic protein

<400> SEQUENCE: 20

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Glu Ser
            35                  40                  45

Lys Tyr Gly Pro Pro Cys Pro Pro Cys Pro Ala Pro Glu Ala Ala Gly
50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
            100                 105                 110

His Asn Ala Lys Thr Lys Pro Arg Glu Glu Gln Phe Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
```

```
                165                 170                 175
Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Gly Gly Gly Ser Gly Gly Gly Ser Gly Gly Gly Gly
        275                 280                 285

Ser His Pro Ile Pro Asp Ser Ser Pro Leu Leu Gln Phe Gly Gly Gln
    290                 295                 300

Val Arg Gln Arg Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
            340                 345                 350

Gln Ile Leu Gly Val Lys Thr Ser Arg Phe Leu Cys Gln Arg Pro Asp
        355                 360                 365

Gly Ala Leu Tyr Gly Ser Leu His Phe Asp Pro Glu Ala Cys Ser Phe
    370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
            420                 425                 430

Pro Ala Leu Pro Glu Pro Pro Gly Ile Leu Ala Pro Gln Pro Pro Asp
        435                 440                 445

Val Gly Ser Ser Asp Pro Leu His Met Val Gly Ala Ser Gln Gly Leu
    450                 455                 460

Ser Pro Ser Tyr Ala Ser
465                 470

<210> SEQ ID NO 21
<211> LENGTH: 470
<212> TYPE: PRT
<213> ORGANISM: Artificial Sequence
<220> FEATURE:
<223> OTHER INFORMATION: Description of artificial sequence: synthetic
      protein

<400> SEQUENCE: 21

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Gly Ser Glu Ser
        35                  40                  45
```

```
Lys Tyr Gly Pro Pro Cys Pro Cys Pro Ala Pro Glu Ala Ala Gly
 50                  55                  60

Gly Pro Ser Val Phe Leu Phe Pro Pro Lys Pro Lys Asp Thr Leu Met
 65                  70                  75                  80

Ile Ser Arg Thr Pro Glu Val Thr Cys Val Val Val Asp Val Ser Gln
                 85                  90                  95

Glu Asp Pro Glu Val Gln Phe Asn Trp Tyr Val Asp Gly Val Glu Val
             100                 105                 110

His Asn Ala Lys Thr Lys Pro Arg Glu Glu Gln Phe Asn Ser Thr Tyr
         115                 120                 125

Arg Val Val Ser Val Leu Thr Val Leu His Gln Asp Trp Leu Asn Gly
 130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                 165                 170                 175

Tyr Thr Leu Pro Pro Ser Gln Glu Glu Met Thr Lys Asn Gln Val Ser
             180                 185                 190

Leu Thr Cys Leu Val Lys Gly Phe Tyr Pro Ser Asp Ile Ala Val Glu
         195                 200                 205

Trp Glu Ser Asn Gly Gln Pro Glu Asn Asn Tyr Lys Thr Thr Pro Pro
 210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                 245                 250                 255

His Glu Ala Leu His Asn His Tyr Thr Gln Lys Ser Leu Ser Leu Ser
             260                 265                 270

Leu Gly Gly Gly Gly Ser Gly Gly Gly Ser Gly Gly Gly
         275                 280                 285

Ser His Pro Ile Pro Asp Ser Ser Pro Leu Leu Gln Phe Gly Gly Gln
 290                 295                 300

Val Arg Gln Arg Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                 325                 330                 335

Ser Pro Glu Ser Leu Leu Gln Leu Lys Ala Leu Lys Pro Gly Val Ile
             340                 345                 350

Gln Ile Leu Gly Val Lys Thr Ser Arg Phe Leu Cys Gln Arg Pro Asp
         355                 360                 365

Gly Ala Leu Tyr Gly Ser Leu His Phe Asp Pro Glu Ala Cys Ser Phe
 370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                 405                 410                 415

Pro Ala Pro Arg Gly Pro Ala Arg Phe Leu Pro Leu Pro Gly Leu Pro
             420                 425                 430

Pro Ala Leu Pro Glu Pro Pro Gly Ile Leu Ala Pro Gln Pro Pro Asp
         435                 440                 445

Val Gly Ser Ser Asp Pro Leu Ser Met Val Glu Ala Leu Gln Gly Arg
450                 455                 460

Ser Pro Ser Tyr Ala Ser
```

```
465            470
```

<210> SEQ ID NO 22
<211> LENGTH: 470
<212> TYPE: PRT
<213> ORGANISM: Artificial Sequence
<220> FEATURE:
<223> OTHER INFORMATION: Description of artificial sequence: synthetic
      protein

<400> SEQUENCE: 22

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Ser Gly Gly Gly Ser Glu Ser
            35                  40                  45

Lys Tyr Gly Pro Pro Cys Pro Pro Cys Pro Ala Pro Glu Ala Ala Gly
50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Gly Gly Gly Gly Ser Gly Gly Gly Gly Ser Gly Gly Gly Gly
        275                 280                 285

Ser His Pro Ile Pro Asp Ser Ser Pro Leu Leu Gln Phe Gly Gly Gln
290                 295                 300

Val Arg Gln Arg Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
            340                 345                 350
```

```
Gln Ile Leu Gly Val Lys Thr Ser Arg Phe Leu Cys Gln Arg Pro Asp
        355                 360                 365

Gly Ala Leu Tyr Gly Ser Leu His Phe Asp Pro Glu Ala Cys Ser Phe
    370                 375                 380

Arg Glu Leu Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
            420                 425                 430

Pro Ala Leu Pro Glu Pro Pro Gly Ile Leu Ala Pro Gln Pro Pro Asp
            435                 440                 445

Val Gly Ser Ser Asp Pro Leu Ser Met Val Gly Pro Ser Gln Gly Arg
    450                 455                 460

Ser Pro Ser Tyr Ala Ser
465                 470

<210> SEQ ID NO 23
<211> LENGTH: 1272
<212> TYPE: DNA
<213> ORGANISM: Artificial Sequence
<220> FEATURE:
<223> OTHER INFORMATION: DNA-S1F1

<400> SEQUENCE: 23
gagtctaagt acggccctcc ctgccctcct tgtcctgctc ctgaagctgc tggcggccct      60
tccgtgttcc tgttccccccc aaagcccaag acaccctga tgatctcccg accccccgaa     120
gtgacctgcg tggtggtgga tgtgtcccag gaagatcccg aggtgcagtt caattggtac     180
gtggacggcg tggaagtgca caacgccaag accaagccca gaggaacaa gttcaactcc      240
acctaccggg tggtgtccgt gctgacagtg ctgcaccagg actggctgaa cggcaaagag     300
tacaagtgca aggtgtccaa caagggcctg cccagctcca tcgaaaagac catctccaag     360
gccaagggcc agccccggga accccaggtg tacacactgc ctccaagcca ggaagagatg     420
accaagaacc aggtgtccct gacctgtctc gtgaaaggct tctaccccctc cgatatcgcc     480
gtggaatggg agtccaacgg ccagcctgag aacaactaca agaccacccc ccctgtgctg     540
gactccgacg gctccttctt cctgtactcc aagctgaccg tggacaagtc cagatggcag     600
gaaggcaacg tgttctcctg ctccgtgatg cacgaggccc tgcacaacca ctacacccag     660
aagtccctgt ccctgtctct gggaggcggc ggaggatctg gcggaggtgg aagcggaggc     720
ggtggatctc accccatccc cgacagcagc cccctgctgc agttcggcgg ccaggtgagg     780
cagaggtacc tgtacaccga cgacgcccag cagaccgagg cccacctgga gatcaggag      840
gacggcaccg tgggcggcgc cgccgaccag agccccgaga gcctgctgca gctgaaggcc     900
ctgaagcccg gcgtgatcca gatcctgggc gtgaagacca gcaggttcct gtgccagagg     960
cccgacggcg ccctgtacgg cagcctgcac ttcgaccccg aggcctgcag cttcagggag    1020
aggctgctgg aggacggcta caacgtgtac cagagcgagg cccacggcct gcccctgcac    1080
ctgcccggca acaagagccc cacaggac cccgccccca ggggccccgc caggttcctg     1140
cccctgcccg gcctgccccc cgccctgccc gagccccccg gcatcctggc ccccagccc     1200
cccgacgtgg gcagcagcga ccccctgagc atggtgggag atcccaggg caggagcccc    1260
agctacgcca gc                                                       1272
```

```
<210> SEQ ID NO 24
<211> LENGTH: 1410
<212> TYPE: DNA
<213> ORGANISM: Artificial Sequence
<220> FEATURE:
<223> OTHER INFORMATION: DNA-D1F1

<400> SEQUENCE: 24
catggcgagg gcacctttac ctccgacgtg tcctcctacc tggaagaaca ggccgccaaa      60
gagtttatcg cctggctcgt gaagggcggt ggtggcggcg aggatctgg cggaggtgga     120 agcggaggcg gtggatctga gtctaagtac ggccctccct gccctccttg tcctgctcct    180
gaagctgctg gcggcccttc cgtgttcctg ttcccccaa agcccaagga caccctgatg    240
atctcccgga cccccgaagt gacctgcgtg gtggtggatg tgtcccagga agatcccgag    300
gtgcagttca attggtacgt ggacggcgtg gaagtgcaca acgccaagac caagcccaga    360
gaggaacagt tcaactccac ctaccgggtg gtgtccgtgc tgacagtgct gcaccaggac    420
tggctgaacg gcaaagagta caagtgcaag gtgtccaaca agggcctgcc cagctccatc    480
gaaaagacca ctctccaaggc caagggccag ccccgggaac ccaggtgta cacactgcct    540 ccaagccagg aagagatgac caagaaccag gtgtccctga cctgtctcgt gaaaggcttc    600 taccctccg atatcgccgt ggaatgggag tccaacggcc agcctgagaa caactacaag    660
accacccccc ctgtgctgga ctccgacggc tccttcttcc tgtactccaa gctgaccgtg    720
gacaagtcca gatggcagga aggcaacgtg ttctcctgct ccgtgatgca cgaggccctg    780
cacaaccact acacccagaa gtccctgtcc ctgtctctgg gaggcggcgg aggatctggc    840
ggaggtggaa gcggaggcgg tggatctcac cccatccccg acagcagccc cctgctgcag    900
ttcggcggcc aggtgaggca gaggtacctg tacaccgacg acgcccagca gaccgaggcc    960
cacctggaga tcagggagga cggcaccgtg ggcggcgccg ccgaccagag ccccgagagc   1020
ctgctgcagc tgaaggccct gaagcccggc gtgatccaga tcctgggcgt gaagaccagc   1080
aggttcctgt gccagaggcc cgacggcgcc ctgtacggca gcctgcactt cgaccccgag   1140
gcctgcagct tcagggagag gctgctggag gacggctaca acgtgtacca gagcgaggcc   1200
cacggcctgc ccctgcacct gcccggcaac aagagccccc acaggaccc cgcccccagg   1260 ggccccgcca ggttcctgcc cctgccccgg ctgccccccg ccctgcccga gccccccggc   1320
atcctggccc ccagccccc cgacgtgggc agcagcgacc ccctgagcat ggtgggagga   1380
tcccagggca ggagccccag ctacgccagc                                    1410

<210> SEQ ID NO 25
<211> LENGTH: 1410
<212> TYPE: DNA
<213> ORGANISM: Artificial Sequence
<220> FEATURE:
<223> OTHER INFORMATION: DNA-D1F2

<400> SEQUENCE: 25
catggcgagg gcacctttac ctccgacgtg tcctcctacc tggaagaaca ggccgccaaa      60
gagtttatcg cctggctcgt gaagggcggt ggtggcggcg aggatctgg cggaggtgga     120 agcggaggcg gtggatctga gtctaagtac ggccctccct gccctccttg tcctgctcct    180
gaagctgctg gcggcccttc cgtgttcctg ttcccccaa agcccaagga caccctgatg    240
atctcccgga cccccgaagt gacctgcgtg gtggtggatg tgtcccagga agatcccgag    300
gtgcagttca attggtacgt ggacggcgtg gaagtgcaca acgccaagac caagcccaga    360
```

```
gaggaacagt tcaactccac ctaccggtg gtgtccgtgc tgacagtgct gcaccaggac      420
tggctgaacg gcaaagagta caagtgcaag gtgtccaaca agggcctgcc cagctccatc      480
gaaaagacca tctccaaggc caagggccag ccccgggaac cccaggtgta cacactgcct      540
ccaagccagg aagagatgac caagaaccag gtgtccctga cctgtctcgt gaaaggcttc      600
tacccctccg atatcgccgt ggaatgggag tccaacggcc agcctgagaa caactacaag      660
accacccccc ctgtgctgga ctccgacggc tccttcttcc tgtactccag gctgaccgtg      720
gacaagtcca gatggcagga aggcaacgtg ttctcctgct ccgtgatgca cgaggccctg      780
cacaaccact acacccagaa gtccctgtcc ctgtctctgg gaggcggcgg aggatctggc      840
ggaggtggaa gcggaggcgg tggatctcac cccatccccg acagcagccc cctgctgcag      900
ttcggcggcc aggtgaggca gaggtacctg tacaccgacg acgcccagca gaccgaggcc      960
cacctggaga tcagggagga cggcaccgtg ggcggcgccg ccgaccagag ccccgagagc      1020
ctgctgcagc tgaaggccct gaagcccggc gtgatccaga tcctgggcgt gaagaccagc      1080
aggttcctgt gccagaggcc cgacggcgcc ctgtacggca gcctgcactt cgaccccgag      1140
gcctgcagct tcagggagag gctgctggag gacggctaca cgtgtaccga gagcgaggcc      1200
cacggcctgc ccctgcacct gcccggcaac aagagccccc acaggaccc cgcccccagg      1260 ggccccgcca ggttcctgcc cctgcccggc ctgcccccg cctgcccga gccccccggc      1320 atcctggccc ccagccccc cgacgtgggc agcagcgacc ccctgagcat ggtgggagga      1380
tcccagggca ggagccccag ctacgccagc                                      1410
```

<210> SEQ ID NO 26
<211> LENGTH: 1410
<212> TYPE: DNA
<213> ORGANISM: Artificial Sequence
<220> FEATURE:
<223> OTHER INFORMATION: DNA-D2F1

<400> SEQUENCE: 26

```
catggcgagg gcacctttac ctccgacgtg tcctcctacc tggaagaaca ggccgccaaa       60
gagtttatcg cctggctcgt gaagggcggt ggtggcggcg aggatctggg cggaggtgga      120
agcggaggcg gtggatctga gtctaagtac ggccctccct gccctccttg tcctgctcct      180
gaagctgctg gcggcccttc cgtgttcctg ttcccccaa agcccaagga caccctgatg      240
atctcccgga cccccgaagt gacctgcgtg gtggtggatg tgtcccagga agatcccgag      300
gtgcagttca attggtacgt ggacggcgtg gaagtgcaca acgccaagac caagcccaga      360
gaggaacagt tcaactccac ctaccgggtg gtgtccgtgc tgacagtgct gcaccaggac      420
tggctgaacg gcaaagagta caagtgcaag gtgtccaaca agggcctgcc cagctccatc      480
gaaaagacca tctccaaggc caagggccag ccccgggaac cccaggtgta cacactgcct      540
ccaagccagg aagagatgac caagaaccag gtgtccctga cctgtctcgt gaaaggcttc      600
tacccctccg atatcgccgt ggaatgggag tccaacggcc agcctgagaa caactacaag      660
accacccccc ctgtgctgga ctccgacggc tccttcttcc tgtactccaa gctgaccgtg      720
gacaagtcca gatggcagga aggcaacgtg ttctcctgct ccgtgatgca cgaggccctg      780
cacaaccact acacccagaa gtccctgtcc ctgtctctgg gaggcggcgg aggatctggc      840
ggaggtggaa gcggaggcgg tggatctcac cccatccccg acagcagccc cctgctgcag      900
ttcggcggcc aggtgaggca gaggtacctg tacaccgacg acgcccagca gaccgaggcc      960
cacctggaga tcagggagga cggcaccgtg ggcggcgccg ccgaccagag ccccgagagc     1020
```

```
ctgctgcagc tgaaggccct gaagcccggc gtgatccaga tcctgggcgt gaagaccagc      1080
aggttcctgt gccagaggcc cgacggcgcc ctgtacggca gcctgcactt cgaccccgag      1140
gcctgcagct tcagggagag gctgctggag gacggctaca acgtgtacca gagcgaggcc      1200
cacggcctgc ccctgcacct gcccggcaac aagagccccc acaggaccc cgcccccagg       1260 ggccccgcca ggttcctgcc cctgcccggc ctgcccccg cctgcccga gcccccggc         1320 atcctggccc ccagccccc cgacgtgggc agcagcgacc ccctgagcat ggtgggagga       1380
tcccagggca ggagccccag cttcgccagc                                       1410
```

<210> SEQ ID NO 27
<211> LENGTH: 1410
<212> TYPE: DNA
<213> ORGANISM: Artificial Sequence
<220> FEATURE:
<223> OTHER INFORMATION: DNA-D3F1

<400> SEQUENCE: 27

```
catggcgagg gcacctttac ctccgacgtg tcctcctacc tggaagaaca ggccgccaaa      60
gagtttatcg cctggctcgt gaagggcggt ggtggcggcg aggatctgg cggaggtgga      120 agcggaggcg gtggatctga gagcaagtac ggccccccct gtcctccttg ccccgcccct      180
gaggccgccg cgcccctag cgtgtttctg tttccccca agcctaaaga cacctgatg        240 atctccagga cccctgaggt gacctgtgtg gtggtggacg tgagccagga ggaccccgag      300
gtgcagttca actggtacgt ggatggcgtg aagtgcaca acgccaagac caagcccagg       360
gaggagcaat tcaacagcac ctacagggtg gtgagcgtcc tcaccgtcct gcatcaggac      420
tggctgaacg gcaaggagta caagtgcaaa gtgtccaaca agggcctgcc ttcctccatc      480
gagaagacca tctccaaggc taagggccag cccagggaac ccaagtgta ccctccccc      540 ccctcccagg aggagatgac caaaaaccaa gtctccctga cctgcctggt gagggcttc      600 taccctccg atattgccgt cgagtgggag agcaacggcc agcccgagaa caactataag       660 accaccccc ccgtgctgga ttccgacggt tcttttttcc tgtatagcaa gctgaccgtg       720
gacaagtcca ggtggcagga gggcaacgtg ttctcctgca gcgtgatgca cgaggccctc      780
cacaaccact acacccagaa atccctgtcc ctgtccctcg gcggcggagg cggctccggc      840
ggcggcggca gcgaggcgg aggaagccat cccattcccg actccagccc cctgctgcag      900
tttggcggcc aagtgaggca gagatacctg tacaccgacg atgcccaaca gacagaggct      960
cacctggaaa tcagggagga cggcaccgtg ggcggagctg ctgatcagag ccccgagtcc     1020
ctcctccagc tgaaggccct gaagcccgga gtgatccaga tcctgggcgt gaagacatcc     1080
aggttcctgt gccagagacc cgatggcgcc ctgtacggaa gcctgcactt cgaccccgag     1140
gcttgctcct tcagggagag gctgctggag gacggctaca acgtgtacca gtccgaggct     1200
cacggactcc ctctgcacct gcctggcaac aagagccctc acagagaccc cgcccctaga     1260
ggccctgcta ggtttctgcc cctgcctggc ctgcctcctg ctctgcccga gcccctggt     1320 attttagctc ctcagcctcc cgatgtggga agcagcgacc ccctgagcat ggtgggagct     1380
agccagggca ggagccctag ctacgccagc                                      1410
```

<210> SEQ ID NO 28
<211> LENGTH: 1410
<212> TYPE: DNA
<213> ORGANISM: Artificial Sequence
<220> FEATURE:

<223> OTHER INFORMATION: DNA-D4F1

<400> SEQUENCE: 28

| | | |
|---|---|---|
| catggcgagg gcacctttac ctccgacgtg tcctcctacc tggaagaaca ggccgccaaa | 60 | |
| gagtttatcg cctggctcgt gaagggcggt ggtggcggcg aggatctgg cggaggtgga | 120 | |
| agcggaggcg gtggatctga gagcaagtac ggcccccct gtcctccttg cccgcccct | 180 | |
| gaggccgccg gcggccctag cgtgtttctg tttccccca agcctaaaga cccctgatg | 240 | |
| atctccagga cccctgaggt gacctgtgtg gtggtggacg tgagccagga ggaccccgag | 300 | |
| gtgcagttca actggtacgt ggatggcgtg gaagtgcaca acgccaagac caagcccagg | 360 | |
| gaggagcaat tcaacagcac ctacagggtg gtgagcgtcc tcaccgtcct gcatcaggac | 420 | |
| tggctgaacg gcaaggagta caagtgcaaa gtgtccaaca agggcctgcc ttcctccatc | 480 | |
| gagaagacca tctccaaggc taagggccag cccagggaac ccaagtgta cccctcccc | 540 | |
| ccctcccagg aggagatgac caaaaaccaa gtctccctga cctgcctggt gaagggcttc | 600 | |
| taccctccg atattgccgt cgagtgggag agcaacggcc agcccgagaa caactataag | 660 | |
| accaccccc ccgtgctgga ttccgacggt tcttttttcc tgtatagcaa gctgaccgtg | 720 | |
| gacaagtcca ggtggcagga gggcaacgtg ttctcctgca cgtgatgca cgaggccctc | 780 | |
| cacaaccact acacccagaa atccctgtcc ctgtccctcg cggcggagg cggctccggc | 840 | |
| ggcggcggca gcggaggcgg aggaagcat cccattcccg actccagccc cctgctgcag | 900 | |
| tttggcggcc aagtgaggca gagatacctg tacaccgacg atgcccaaca gacagaggct | 960 | |
| cacctggaaa tcagggagga cggcaccgtg ggcggagctg ctgatcagag ccccgagtcc | 1020 | |
| ctcctccagc tgaaggccct gaagcccgga gtgatccaga tcctgggcgt gaagacatcc | 1080 | |
| aggttcctgt gccagagacc cgatggcgcc ctgtacggaa gcctgcactt cgaccccgag | 1140 | |
| gcttgctcct tcagggagag gctgctggag gacggctaca acgtgtacca gtccgaggct | 1200 | |
| cacggactcc ctctgcacct gcctggcaac aagagccctc acagagaccc cgcccctaga | 1260 | |
| ggccctgcta ggtttctgcc cctgcctggc ctgcctcctg ctctgccga gccccctggt | 1320 | |
| attttagctc ctcagcctcc cgatgtggga agcagcgacc ccctgcacat ggtgggagct | 1380 | |
| agccagggca ggagccctag ctacgccagc | 1410 | |

<210> SEQ ID NO 29
<211> LENGTH: 1410
<212> TYPE: DNA
<213> ORGANISM: Artificial Sequence
<220> FEATURE:
<223> OTHER INFORMATION: DNA-D5F1

<400> SEQUENCE: 29

| | | |
|---|---|---|
| catggcgagg gcacctttac ctccgacgtg tcctcctacc tggaagaaca ggccgccaaa | 60 | |
| gagtttatcg cctggctcgt gaagggcggt ggtggcggcg aggatctgg cggaggtgga | 120 | |
| agcggaggcg gtggatctga gagcaagtac ggcccccct gtcctccttg cccgcccct | 180 | |
| gaggccgccg gcggccctag cgtgtttctg tttccccca agcctaaaga cccctgatg | 240 | |
| atctccagga cccctgaggt gacctgtgtg gtggtggacg tgagccagga ggaccccgag | 300 | |
| gtgcagttca actggtacgt ggatggcgtg gaagtgcaca acgccaagac caagcccagg | 360 | |
| gaggagcaat tcaacagcac ctacagggtg gtgagcgtcc tcaccgtcct gcatcaggac | 420 | |
| tggctgaacg gcaaggagta caagtgcaaa gtgtccaaca agggcctgcc ttcctccatc | 480 | |
| gagaagacca tctccaaggc taagggccag cccagggaac ccaagtgta cccctcccc | 540 | |

```
ccctcccagg aggagatgac caaaaaccaa gtctccctga cctgcctggt gaagggcttc    600 taccccctccg atattgccgt cgagtgggag agcaacggcc agcccgagaa caactataag    660
accacccccc ccgtgctgga ttccgacggt tcttttttcc tgtatagcaa gctgaccgtg    720
gacaagtcca ggtggcagga gggcaacgtg ttctcctgca gcgtgatgca cgaggccctc    780
cacaaccact acacccagaa atccctgtcc ctgtccctcg gcggcggagg cggctccggc    840
ggcggcggca gcggaggcgg aggaagccat cccattcccg actccagccc cctgctgcag    900
tttggcggcc aagtgaggca gagatacctg tacaccgacg atgcccaaca gacagaggct    960
cacctggaaa tcagggagga cggcaccgtg ggcggagctg ctgatcagag ccccgagtcc    1020
ctcctccagc tgaaggccct gaagcccgga gtgatccaga tcctgggcgt gaagacatcc    1080
aggttcctgt gccagagacc cgatggcgcc ctgtacggaa gctgcactt cgaccccgag    1140 gcttgctcct tcagggagag gctgctggag gacggctaca acgtgtacca gtccgaggct    1200
cacggactcc ctctgcacct gcctggcaac aagagccctc acagagaccc cgccctaga    1260 ggccctgcta ggtttctgcc cctgcctggc ctgcctcctg ctctgcccga gccccctggt    1320
attttagctc ctcagcctcc cgatgtggga agcagcgacc ccctgcacat ggtgggagct    1380
agccagggcc tgagccctag ctacgccagc                                     1410

<210> SEQ ID NO 30
<211> LENGTH: 1410
<212> TYPE: DNA
<213> ORGANISM: Artificial Sequence
<220> FEATURE:
<223> OTHER INFORMATION: DNA-D6F1

<400> SEQUENCE: 30
catggcgagg gcacctttac ctccgacgtg tcctcctacc tggaagaaca ggccgccaaa     60
gagtttatcg cctggctcgt gaagggcggt ggtggcggcg gaggatctgg cggaggtgga    120
agcggaggcg gtggatctga gtctaagtac ggccctccct gccctccttg tcctgctcct    180
gaagctgctg gcggcccttc cgtgttcctg ttcccccaa agcccaagga caccctgatg    240
atctccggaa cccccgaagt gacctgcgtg gtggtggatg tgtcccagga agatcccgag    300
gtgcagttca attggtacgt ggacggcgtg gaagtgcaca acgccaagac caagcccaga    360
gaggaacagt tcaactccac ctaccgggtg gtgtccgtgc tgacagtgct gcaccaggac    420
tggctgaacg gcaaagagta caagtgcaag gtgtccaaca agggcctgcc cagctccatc    480
gaaaagacca ctctccaagg ccaagggcag cccggaaac cccaggtgta cactactgct    540
ccaagccagg aagagatgac caagaaccag gtgtccctga cctgtctcgt gaaaggcttc    600 taccccctccg atatcgccgt ggaatgggag tccaacggcc agcctgagaa caactacaag    660
accacccccc ctgtgctgga ctccgacggc tccttcttcc tgtactccaa gctgaccgtg    720
gacaagtcca gatggcagga aggcaacgtg ttctcctgct ccgtgatgca cgaggccctg    780
cacaaccact acacccagaa gtccctgtcc ctgtctctgg gaggcggcgg aggatctggc    840
ggaggtggaa gcggaggcgg tggatctcac cccatccccg acagcagccc cctgctgcag    900
ttcggcggcc aggtgaggca gaggtacctg tacaccgacg acgcccagca gaccgaggcc    960
cacctggaga tcagggagga cggcaccgtg ggcggcgccg ccgaccagag ccccgagagc    1020
ctgctgcagc tgaaggccct gaagcccggc gtgatccaga tcctgggcgt gaagaccagc    1080
aggttcctgt gccagaggcc cgacggcgcc ctgtacggca gctgcactt cgaccccgag    1140
```

```
gcctgcagct tcagggagag gctgctggag gacggctaca acgtgtacca gagcgaggcc    1200
cacggcctgc ccctgcacct gcccggcaac aagagccccc acaggaccc cgccccagg      1260 ggccccgcca ggttcctgcc cctgcccggc ctgcccccg ccctgcccga gccccccggc     1320
atcctggccc cccagccccc cgacgtgggc agcagcgacc ccctgagcat ggtggaggcc    1380
ctgcagggca ggagccccag ctacgccagc                                     1410
```

<210> SEQ ID NO 31
<211> LENGTH: 1410
<212> TYPE: DNA
<213> ORGANISM: Artificial Sequence
<220> FEATURE:
<223> OTHER INFORMATION: DNA-D7F1

<400> SEQUENCE: 31

```
catggcgagg gcacctttac ctccgacgtg tcctcctacc tggaagaaca ggccgccaaa     60
gagtttatcg cctggctcgt gaagggcggt ggtggcggcg gaggatctgg cggaggtgga    120
agcggaggcg gtggatctga gtctaagtac ggccctccct gccctccttg tcctgctcct    180
gaagctgctg gcggcccttc cgtgttcctg ttccccccaa agcccaagga caccctgatg    240
atctcccgga cccccgaagt gacctgcgtg gtggtggatg tgtcccagga agatcccgag    300
gtgcagttca attggtacgt ggacggcgtg gaagtgcaca acgccaagac caagcccaga    360
gaggaacagt tcaactccac ctaccgggtg gtgtccgtgc tgaccagtgc tgcaccagga    420 ctggctgaacg gcaaagagta caagtgcaag gtgtccaaca ggcctgcc agctccatc     480 gaaaagacca ctccaaggc caaggccag ccccgggaac cccaggtgta cacactgcct     540
ccaagccagg aagagatgac caagaaccag gtgtccctga cctgtctcgt gaaaggcttc   600
tacccctccg atatcgccgt ggaatgggag tccaacggcc agcctgagaa caactacaag    660 accaccccc ctgtgctgga ctccgacggc tccttcttcc tgtactccaa gctgaccgtg    720
gacaagtcca gatggcagga aggcaacgtg ttctcctgct ccgtgatgca cgaggccctg    780
cacaaccact acacccagaa gtccctgtcc ctgtctctgg gaggcggcgg aggatctggc    840
ggaggtggaa gcggaggcgg tggatctcac cccatccccg acagcagccc cctgctgcag   900
ttcggcggcc aggtgaggca gaggtacctg tacaccgacg acgcccagca gaccgaggcc    960
cacctggaga tcaggagga cggcaccgtg ggcggcgccg ccgaccagag ccccgagagc   1020
ctgctgcagc tgaaggccct gaagcccggc gtgatccaga tcctgggcgt gaagaccagc   1080
aggttcctgt gccagaggcc cgacggcgcc ctgtacggca gcctgcactt cgaccccgag   1140
gcctgcagct tcagggagct gctgctggag gacggctaca acgtgtacca gagcgaggcc   1200
cacggcctgc ccctgcacct gcccggcaac aagagccccc acaggaccc cgccccagg    1260 ggccccgcca ggttcctgcc cctgcccggc ctgcccccg ccctgcccga gccccccggc    1320
atcctggccc cccagccccc cgacgtgggc agcagcgacc ccctgagcat ggtgggacct   1380
tcccagggca ggagccccag ctacgccagc                                   1410
```

<210> SEQ ID NO 32
<211> LENGTH: 10
<212> TYPE: PRT
<213> ORGANISM: Artificial Sequence
<220> FEATURE:
<223> OTHER INFORMATION: Description of artificial sequence: synthetic
      protein

<400> SEQUENCE: 32

```
Gly Gly Gly Gly Ser Gly Gly Gly Gly Ser
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Description of artificial sequence: synthetic
      protein

<400> SEQUENCE: 33

Gly Gly Gly Gly Ser Gly Gly Gly Gly Ser Gly Gly Gly Gly Ser Ala
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of artificial sequence: synthetic
      protein

<400> SEQUENCE: 34

Gly Gly Gly Gly Gly Ser Gly Gly Gly Ser Gly Gly Gly Gly Ser
1               5                   10                  15

<210> SEQ ID NO 35
<211> LENGTH: 8
<212> TYPE: PRT
<213> ORGANISM: Artificial Sequence
<220> FEATURE:
<223> OTHER INFORMATION: Description of artificial sequence: synthetic
      protein

<400> SEQUENCE: 35

Gly Gly Gly Lys Gly Gly Gly Gly
1               5

<210> SEQ ID NO 36
<211> LENGTH: 8
<212> TYPE: PRT
<213> ORGANISM: Artificial Sequence
<220> FEATURE:
<223> OTHER INFORMATION: Description of artificial sequence: synthetic
      protein

<400> SEQUENCE: 36

Gly Gly Gly Asn Gly Ser Gly Gly
1               5

<210> SEQ ID NO 37
<211> LENGTH: 8
<212> TYPE: PRT
<213> ORGANISM: Artificial Sequence
<220> FEATURE:
<223> OTHER INFORMATION: Description of artificial sequence: synthetic
      protein

<400> SEQUENCE: 37

Gly Gly Gly Cys Gly Gly Gly Gly
1               5

<210> SEQ ID NO 38
<211> LENGTH: 5
<212> TYPE: PRT
<213> ORGANISM: Artificial Sequence
<220> FEATURE:
```

```
<223> OTHER INFORMATION: Description of artificial sequence: synthetic
      protein

<400> SEQUENCE: 38

Gly Pro Asn Gly Gly
1               5
```

DUAL-TARGET FUSION PROTEINS COMPRISING FGF21 AND GLP-1, CONNECTED THROUGH A Fc PORTION OF AN IMMUNOGLOBULIN

CROSS REFERENCE TO RELATED APPLICATIONS

This is a U.S. national stage application of the International Patent Application No. PCT/CN2018/078925, filed Mar. 14, 2018, which claims priorities to Chinese Patent Application No. 201710148158.7, filed Mar. 14, 2017, and No. 201810129427.X, filed Feb. 8, 2018, all of which are incorporated herein by reference in their entirety.

FIELD OF THE INVENTION

The present invention relates to fusion proteins comprising fibroblast growth factor 21 (FGF21) and glucagon-like peptide-1 (GLP-1), connected through an immunoglobulin Fc portion, and uses of the fusion proteins to treat metabolic diseases.

BACKGROUND OF THE INVENTION

At present, there are three categories of drugs for the treatment of diabetes: oral small molecule drugs, insulin and GLP-1 receptor agonist drugs. Long-term treatment of small molecule drugs leads to obvious side effects, and post-diabetic glycemic control is not satisfactory. Treatment of diabetes with insulin requires multiple injections (at least once daily), and hypoglycemia is easily triggered by differences in individual dosages. A single GLP-1 receptor agonist is not a first-line agent and has limited efficacy in cardiovascular complications caused by abnormal metabolism of diabetes.

Glucagon-like peptide-1 (GLP-1) is a type of incretin secreted by intestinal L cells. It stimulates islet ß-cells to secrete insulin, maintaining insulin balance in patients. Natural GLP-1 survives only up to 2 minutes in vitro and therefore is not effective as a drug. For a few years now, several parties including Eli Lilly, Novo Nordisk, GSK have been competitively seeking to transform the protein in order to obtain a long-acting GLP-1 class of hypoglycemic drugs. Currently, the longest-acting of GLP-1 drugs, such as dulaglutide, can be administered once per week by fusing an antibody fragment to the GLP-1 protein. However, studies find that the glucose-lowering curve of dulaglutide is not stable, and blood glucose begins to rise on the day after treatment. Thus, this situation is not ideal for controlling diabetes, and it may lead to a variety of complications.

Type 2 diabetes has two major hallmarks: peripheral insulin resistance and impaired glucose-dependent insulin secretion of pancreatic beta cells. Metabolic disorders such as diabetes are often caused by a variety of complex factors, so the treatment of multiple metabolic pathways is considered much more advantageous.

Fibroblast growth factor 21 (FGF21) is a recently discovered cytokine. It can stimulate GLUT1 receptors and promote glucose transport into cells, so it may be used as a drug to treat diabetes. However, FGF21 faces a huge problem when it comes to medicinal properties. FGF21 has a short half-life, about one hour in a mouse model (but maximum bioactivity can be maintained for more than six hours). The reason FGF21 rapidly degrades is because of proteases in the body and its propensity to form aggregates in vitro resulting in immunogenicity that is detrimental to half-life extension.

In recent years, various attempts have been made to increase the stability of FGF21 in vivo in order to develop the pharmaceutical use of FGF21, such as mutating at different sites, inserting amino acids/fatty chains, or deleting some amino acids which were made on the basis of FGF21 native sequences, such as those published in WO 2003011213, WO 2005072769, WO 2005061712, WO 2006065582, WO 2010065439, WO2013052311, WO 2013188182, WO 2013033452, WO 2005091944, WO 2012066075, WO 2013188181.

SUMMARY

The present disclosure provides a dual-target fusion protein comprising GLP-1 and FGF21, with differing mutation sites from previously disclosed fusion proteins. The inventors have surprisingly found that the dual-target fusion protein of the present invention has better stability and significantly prolonged half-life, and exhibits synergistic effects in reducing blood sugar, lipid, weight, and so on.

In one aspect of the present invention, there is provided a fusion protein, which comprises or consists of a first polypeptide: GLP-1 or an analogue thereof, a second polypeptide: an IgG4 Fc portion and a third polypeptide: FGF21 or a variant thereof, wherein the first polypeptide is linked to the second polypeptide via a first linker and the third polypeptide is linked to the second polypeptide via a second linker, and wherein serine at position 228 of the IgG4 Fc portion is replaced by proline and arginine at position 409 of the IgG4 Fc portion is replaced by lysine, as compared to a wild-type IgG4 Fc portion. Therefore, the safety and stability of the fusion protein is increased, leading to a significantly prolonged half-life.

The first polypeptide, the GLP-1 analogue, comprises the native GLP-1 sequence (SEQ ID NO: 14) having 1 to 10 (such as 1, 2, 3, 4, 5, 6, 7, 8, 9 or 10) amino acid substitutions, deletions or insertions, thereby prolonging the half-life of GLP-1 in vivo, while retaining or enhancing the biological activity of GLP-1.

In some embodiments, the GLP-1 analogue comprises or consists of an amino acid sequence of SEQ ID NO: 7 (HX1EGTFTSDV SSYLEX2QAAK EFIAWLX3X4GX5 X6), wherein X1 is selected from G or V; X2 is selected from E or G; X3 is selected from V or K; X4 is selected from K or N; X5 is selected from G or E; X6 is selected from G or P or absent.

In other embodiments, the GLP-1 analogue comprises or consists of an amino acid sequence of SEQ ID NO: 1.

The second polypeptide, in some embodiments, the IgG4 Fc portion further comprises any one or more mutations selected from the following: E233P, F234V or F234A, L235E or L235A, N297A, K447 as compared to a wild-type IgG4 Fc portion.

In other embodiments, the IgG4 Fc portion comprises any one of the following combination of mutations:
1) S228P and R409K;
2) S228P, E233P and R409K;
3) S228P, N297A and R409K;
4) S228P, F234A, L235A and R409K;
5) S228P, F234V, L235E and R409K; and
6) S228P, F234A, L235A, R409K and K447, as compared to a wild-type IgG4 Fc portion.

In still other embodiments, the IgG4 Fc portion comprises or consists of an amino acid sequence of SEQ ID NO: 2.

The third polypeptide, the FGF21 variant, comprises the native FGF21 sequence having one or more amino acid substitutions, deletions or insertions, thereby prolonging the in vivo half-life of FGF21 and preserving or enhancing the biological activity of FGF21.

In some embodiments, the FGF21 variant comprises at least one amino acid mutation at position 170 or position 171 or position 172: the amino acid mutation at position 170 is selected from the group consisting of G170E, G170A, G170C, G170D, G170N, and G170S; the amino acid mutation at position 171 is selected from the group consisting of P171A, P171E, P171H, P171Q, P171T, P171Y, P171W, P171C, P171G, P171S, and P171T; the amino acid mutation at position 172 is selected from the group consisting of S172L, S172I, S172V, S172A, and S172M. In some embodiments, the amino acid mutation at position 170 is selected from the group consisting of G170E, G170A, G170D, and G170S; the amino acid mutation at position 171 is selected from the group consisting of P171A, P171E, P171Q, P171W, P171C, P171G, and P171T; the amino acid mutation at position 172 is selected from the group consisting of S172L, S172V, and S172M. In some embodiments, the amino acid mutation at position 170 is selected from the group consisting of G170E, and G170A; the amino acid mutation at position 171 is selected from the group consisting of P171A, P171C, and P171G; the amino acid mutation at position 172 is S172L.

In some embodiments, the FGF21 variant further comprises one or more mutations at one or more sites selected from the group consisting of 45, 98, 100, 118, 134, 150, 151, 152, 167, 175, 179, and 180. In some embodiments, the amino acid mutation at position 45 is selected from the group consisting of A45K, A45R, A45E, and A45Q; the amino acid mutation at position 98 is selected from the group consisting of L98D, L98R, L98E, L98Q, L98K, and L98T; the amino acid mutation at position 100 is L100K; the amino acid mutation at position 118 is L118C; the amino acid at position 134 is A134C; the amino acid mutation at position 150 is P150A; the amino acid mutation at position 151 is G151A; the amino acid at position 152 is I152V; the amino acid mutation at position 167 is selected from the group consisting of S167H, S167C, and S167R; the amino acid mutation at position 175 is selected from the group consisting of R175L, R175H, and R175P; the amino acid at position 179 is selected from the group consisting of Y179S, Y179A, and Y179F; the amino acid mutation at position 180 is selected from the group consisting of A180S, A180E, and A180G.

In some embodiments, the FGF21 variant further comprises one or more mutations at one or more sites selected from the group consisting of 45, 98, 100, 167, 175, 179, and 180. In some embodiments, the amino acid mutation at position 45 is selected from the group consisting of A45K, A45R, A45E, and A45Q; the amino acid mutation at position 98 is selected from the group consisting of L98D, L98R, L98E, L98Q, L98K, and L98T; the amino acid mutation at position 100 is L100K; the amino acid mutation at position 167 is selected from the group consisting of S167H, and S167C; the amino acid mutation at position 175 is selected from the group consisting of R175L, and R175H; the amino acid at position 179 is selected from the group consisting of Y179S, Y179A, and Y179F; the amino acid mutation at position 180 is selected from the group consisting of A180S, A180E, and A180G.

In other embodiments, the FGF21 variant further comprises one or more mutations at one or more sites selected from the group consisting of 45, 98, 167, 175, 179 and 180. In some embodiments, the amino acid mutation at position 45 is selected from the group consisting of A45K, A45R, A45E, and A45Q; the amino acid mutation at position 98 is selected from an the group consisting of L98D, L98R, L98E, L98Q, L98K, and L98T; the amino acid mutation at position 167 is selected from the group consisting of S167H, and S167C; the amino acid mutation at position 175 is selected from the group consisting of R175L, and R175H; the amino acid at position 179 is selected from the group consisting of Y179S, Y179A, and Y179F; the amino acid mutation at position 180 is selected from the group consisting of A180S, A180E, and A180G.

In other embodiments, the FGF21 variant further comprises one or more mutations at one or more sites selected from the group consisting of 98, 167, 175, and 179. In some embodiments, the amino acid mutation at position 98 is selected from the group consisting of L98D, L98R, L98E, and L98K; the amino acid mutation at position 167 is selected from the group consisting of S167H, and S167C; the amino acid at position 175 is selected from the group consisting of: R175L, R175H; the amino acid mutation at position 179 is selected from the group consisting of Y179S, and Y179F.

In other embodiments, the FGF21 variant further comprises one or more mutations at one or more sites selected from the group consisting of 98, 167, 175, and 179. In some embodiments, the amino acid mutation at position 98 is selected from the group consisting of L98D, and L98R; the amino acid mutation at position 167 is S167H; the amino acid at position 175 is R175L; the amino acid mutation at position 179 is Y179F.

In some embodiments, the FGF21 variant comprises at least amino acid mutations at one or more sites of 98 or 171, wherein the amino acid mutation at position 98 is selected from the group consisting of L98D, and L98R; the amino acid mutation at position 170 is selected from the group consisting of P171A, and P171G. In some embodiments, the FGF21 variant further comprises one or more mutations at one or more sites selected from the group consisting of 167, 175, and 179, wherein the amino acid mutation at position 167 is selected from the group consisting of S167H, and S167C; the amino acid mutation at position 175 is selected from the group consisting of R175L, R175H, and R175P; the amino acid at position 179 is selected from the group consisting of Y179S, and Y179F.

In some embodiments, the FGF21 variant comprises at least amino acid mutations at one or more sites of 98 or 171, wherein, the amino acid mutation at position 98 is L98R; the amino acid mutation at position 170 is selected from the group consisting of P171A, and P171G. In some embodiments, the FGF21 variant further comprises one or more mutations at one or more sites selected from the group consisting of 167, 175, and 179, wherein the amino acid mutation at position 167 is S167H; the amino acid mutation at position 175 is R175L; the amino acid at position 179 is Y179F.

In other embodiments, the FGF21 variant comprises any one of the following combination of mutations:
1) L98R and P171G;
2) L98R and P171A;
3) L98R, P171G and Y179F;
4) L98R, P171G and A180E;
5) L98R, G170E, P171A and S172L;
6) L98R, S167H and P171A; and
7) L98R, S167H, P171A and R175L.

In yet other embodiments, the FGF21 variant further comprises:
a) amino-terminal truncation of not more than 8 amino acid residues;
b) carboxy-terminal truncation of not more than 12 amino acid residues;
c) amino-terminal truncation of not more than 8 amino acid residues and carboxy-terminal truncation of not more than 12 amino acid residues; or
d) carboxy-terminal extension of no more than 6 amino acid residues.

In the present invention, the first polypeptide and the third polypeptide are respectively fused with the IgG4 Fc portion through a first linker and a second linker, and the first linker and/or the second linker comprise a polypeptide of 5 to 50 amino acid residues, and the polypeptide comprises at least 50% G. In some embodiments, the first linker and the second linker each independently comprise 1, 2 or 3 G-rich polypeptides. In other embodiments, the first linker and the second linker are each independently selected from GGGGSGGGGS (SEQ ID NO: 32) or GGGGSGGGGSGGGGS (SEQ ID NO: 13) or GGGGSGGGGSGGGGSA (SEQ ID NO: 33).

In some embodiments, the fusion protein is a homodimeric fusion protein.

In some embodiments, the fusion protein is a non-homodimeric fusion protein.

In another aspect of the invention, polynucleotides are provided that encode the fusion proteins of the invention.

In a further aspect of the invention, there is also provided a vector comprising a polynucleotide of the invention.

In a further aspect of the invention, there is also provided a host cell comprising a vector of the invention.

In a further aspect of the invention, there is also provided a method of preparing a fusion protein of the invention, wherein the method comprises expressing a vector of the invention in a host cell.

In another aspect of the present invention, there is also provided a composition (such as a pharmaceutical composition) comprising the fusion protein of the present invention, and optionally one or more pharmaceutically acceptable adjuvants. Such pharmaceutically acceptable adjuvants include, but are not limited to, pharmaceutically acceptable carriers, excipients, diluents, vehicles, and other adjuvants required in pharmaceutical preparations, or any combination thereof.

The fusion proteins or compositions (e.g., pharmaceutical compositions) of the present invention can be used for the treatment of metabolic diseases. The metabolic diseases may be selected from diabetes, obesity and hepatic steatosis.

In another aspect of the present invention, there is also provided use of the fusion protein of the present invention in the preparation of a pharmaceutical composition. In some embodiments, the pharmaceutical composition is used for the treatment of metabolic diseases. For example, the metabolic diseases may be selected from diabetes, obesity and hepatic steatosis.

In another aspect of the present invention, there is also provided a method of treating metabolic diseases, which comprises administering a therapeutically effective amount of the fusion protein or pharmaceutical composition of the present invention to a subject in need. For example, the metabolic diseases may be selected from diabetes, obesity and hepatic steatosis.

In another aspect of the present invention, there is provided a fusion protein or pharmaceutical composition for the treatment of metabolic diseases. The metabolic disease may be selected from diabetes, obesity and hepatic steatosis.

The fusion protein provided herein has the following advantages: the fusion protein has improved stability and it is safer due to avoiding the dissociation of the dimer and thus avoiding the random combination with the antibody in the body; the fusion protein has a longer half-life, the administration period is greater than one week, and patient compliance is increased; it does not trigger ADCC or CDC effect. In another aspect, the homodimeric fusion protein comprising the first polypeptide, the second polypeptide and the third polypeptide provided herein has unique advantages including a good biological activity in metabolic diseases, a stable hypoglycemic effect because of the unique synergistic effect exerted by the first polypeptide and the third polypeptide, and other biological activities such as good hypolipaemic, weight loss, etc.

EXAMPLES

Figure 1:
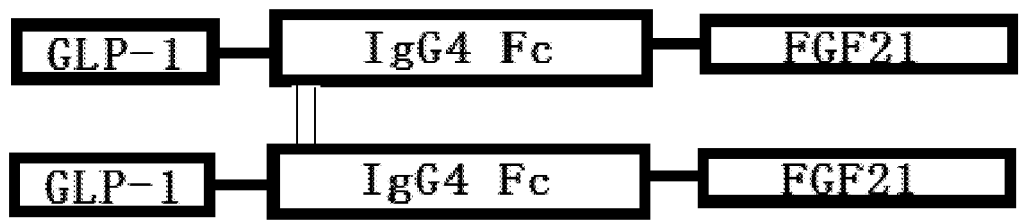
FIG. 1 shows a schematic diagram of a homodimeric fusion protein in one embodiment.

Other features and advantages of the present invention will be apparent from the following detailed description. However, it should be understood that the detailed description and specific examples, while indicating preferred embodiments of the invention, are given by way of illustration only, and in that many changes and modifications within the spirit and scope of the invention will become apparent to those skilled in the art from the detailed description.

DEFINITION OF TERMINOLOGY

As used herein, "native GLP-1 sequence" refers to a native GLP-1 (7-37) sequence with biological activity that is derived from a naturally occurring GLP-1 sequence by excision of an N-terminal 6 peptide. The native GLP-1 sequence, i.e. the native GLP-1 (7-37) sequence, is: HAEGTFTSDV SSYLEGQAAK EFIAWLVKGR G (SEQ ID NO: 14).

As used herein, "biological activity of GLP-1" refers to a variety of biological effects induced by GLP-1, such as stimulating insulin secretion, inhibiting glucagon secretion, inhibiting gastric emptying, inhibiting gastric or intestinal motility and inducing weight loss. A striking feature of GLP-1 is that it can stimulate insulin secretion without risks associated with hypoglycemia.

The "Fc portion" described herein consists of a hinge region of an antibody, CH2 and CH3 constant region structures. The antibody comprises two functionally independent moieties, a variable domain called "Fab" that binds to an antigen, and a constant domain called "Fc" that is involved in effector functions (e.g., complement activation and attack by phagocytes). Fc has a long serum half-life, whereas Fab is short-lived (Capon et al., 1989, Nature 337: 525-31). When linked to a therapeutic protein, the Fc domain may provide longer half-lives or incorporate such functions as Fc receptor binding, protein A binding, complement fixation or even placental transfer (Capon et al., 1989). The term "Fc portion" as used herein refers to wild-type Fc portion sequences derived from natural antibodies (e.g., human IgG1, IgG2, IgG3, or IgG4) and also encompasses their variants. The variants may include one or more amino acid substitutions, additions and/or deletions such as those disclosed herein. In some embodiments, the Fc portion variants maintain the activity of the wild-type Fc portion, such as binding to an Fc receptor.

The amino acid numbers of the IgG4 Fc portion described herein are numbered according to the EU numbering system, for example, "S228P" means that serine at position 228 according to the EU numbering system is replaced by proline; "K447" means that lysine at position 447 according to the EU numbering system is deleted or absent.

The FGF21 wild-type sequence contains 209 amino acids with the NCBI reference sequence number NP_061986.1; a mature FGF21 sequence contains 181 amino acids, and lacks a leader sequence that the FGF21 wild-type contains. As used herein, a "native FGF21 sequence" refers to the mature FGF21 sequence with the following amino acid sequence (SEQ ID NO: 15), the "FGF21 variant" described herein is a mutant polypeptide having the following FGF21 amino acid sequence (SEQ ID NO: 15), the amino acid mutation site numbers are numbered in the following sequence (SEQ ID NO: 15). The amino acid sequence of the FGF21 variant differs from the native FGF21 amino acid sequence by one or more amino acids. FGF21 variants can be obtained by modification with natural or non-naturally occurring amino acids at particular positions in the native FGF21 polypeptide, such modifications include insertion, replacement or deletion of one or more conservative or non-conservative amino acids at a particular position, as well as introduction of non-amino acid structures at specific positions.

SEQ ID NO: 15:
HPIPDSSPLL QFGGQVRQRY LYTDDAQQTE AHLEIREDGT

VGGAADQSPE SLLQLKALKP GVIQILGVKT SRFLCQRPDG

ALYGSLHFDP EACSFRELLL EDGYNVYQSE AHGLPLHLPG

NKSPHRDPAP RGPARFLPLP GLPPALPEPP GILAPQPPDV

GSSDPLSMVG PSQGRSPSYA S

FGF-21 variants may additionally or alternatively comprise deletion of amino acids, which may be N-terminal truncations, C-terminal truncations or internal deletions or any combination thereof. These variants comprising N-terminal truncation, C-terminal truncation and/or internal deletion are referred to as "deletion variants" or "fragments" in the context of the present invention. The terms "deletion variants" and "fragments" are used interchangeably herein. Fragments may be naturally occurring (e.g., splice variants) or artificially constructed, e.g., through genetic means.

"Conservative amino acid substitutions" may include residues of a native amino acid residue (i.e., a residue present at a given position in the wild-type FGF21 polypeptide sequence) replaced by a non-native residue (i.e., a residue not present at a given position in the wild-type FGF21 polypeptide sequence), so that there is little or no effect on the polarity or charge of amino acid residues at this position. Conservative amino acid substitutions also include non-naturally occurring amino acid residues that are commonly incorporated by chemical peptide synthesis rather than by a biological system synthesis. These include peptidomimetics and other reverse forms of amino acid portion.

The naturally occurring residues can be grouped into the following classes based on common side chain properties:
(1) Hydrophobic: norleucine, M, A, V, L, I;
(2) Neutral hydrophilicity: C, S, T;
(3) Acid: D, E;
(4) Alkaline: N, Q, H, K, R;
(5) Residues affecting chain orientation: G, P; and
(6) Aromatic: W, Y, F.

Conservative substitutions may include one member of these categories being exchanged for another member of the same category.

Some conservative amino acid substitutions are shown in the following table:

| Amino acid | conservative amino acid substitutions |
| --- | --- |
| Ala | D-Ala, Gly, Aib, β-Ala, L-Cys, D-Cys |
| Arg | D-Arg, Lys, Orn, D-Orn |

-continued

| Amino acid | conservative amino acid substitutions |
|---|---|
| Asn | D-Asn, Asp, D-Asp, Glu, D-Glu, Gln, D-Gln |
| Asp | D-Asp, D-Asn, Asn, Glu, D-Glu, Gln, D-Gln |
| Cys | D-Cys, S-Me-Cys, Met, D-Met, Thr, D-Thr, L-Ser, D-Ser |
| Gln | D-Gln, Asn, D-Asn, Glu, D-Glu, Asp, D-Asp |
| Glu | D-Glu, Asp, D-Asp, Asn, D-Asn, Gln, D-Gln |
| Gly | Ala, D-Ala, Pro, D-Pro, Aib, β-Ala |
| Ile | D-Ile, Val, D-Val, Leu, D-Leu, Met, D-Met |
| Leu | D-Leu, Val, D-Val, Met, D-Met, Ile, D-Ile |
| Lys | D-Lys, Arg, D-Arg, Orn, D-Orn |
| Met | D-Met, S-Me-Cys, Ile, D-Ile, Leu, D-Leu, Val, D-Val |
| Phe | D-Phe, Tyr, D-Tyr, His, D-His, Trp, D-Trp |
| Pro | D-Pro |
| Ser | D-Ser, Thr, D-Thr, allo-Thr, L-Cys, D-Cys |
| Thr | D-Thr, Ser, D-Ser, allo-Thr, Met, D-Met, Val, D-Val |
| Tyr | D-Tyr, Phe, D-Phe, His, D-His, Tip, D-Trp |
| Val | D-Val, Leu, D-Leu, Ile, D-Ile, Met, D-Met |

Alternatively, the following table lists examples of conservative amino acid substitutions, 0 or more represents that two amino acids are conservative amino acid substitutions between each other:

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 |   |
| F | −4 | −5 | −5 | −3 | −4 | −3 | −6 | −5 | −4 | −5 | −2 | −5 | −4 | −1 | 0 | 1 | 2 | 9 |   |   |
| L | −6 | −4 | −3 | −3 | −2 | −2 | −4 | −3 | −3 | −2 | −2 | −3 | −3 | 2 | 4 | 2 | 6 |   |   |   |
| I | −2 | −3 | −2 | −1 | −1 | 0 | −2 | −2 | −2 | −2 | −2 | −2 | −2 | 4 | 2 | 5 |   |   |   |   |
| M | −5 | −3 | −2 | −2 | −1 | −1 | −3 | −2 | 0 | −1 | −2 | 0 | 0 | 2 | 6 |   |   |   |   |   |
| V | −2 | −1 | −1 | −1 | 0 | 0 | −2 | −2 | −2 | −2 | −2 | −2 | −2 | 4 |   |   |   |   |   |   |
| R | −4 | −3 | 0 | 0 | −2 | −1 | −1 | −1 | 0 | 1 | 2 | 3 | 6 |   |   |   |   |   |   |   |
| K | −5 | −2 | −1 | 0 | −1 | 0 | 0 | 0 | 1 | 1 | 0 | 5 |   |   |   |   |   |   |   |   |
| H | −3 | −2 | 0 | −1 | −1 | −1 | 1 | 1 | 2 | 3 | 6 |   |   |   |   |   |   |   |   |   |
| Q | −5 | −1 | 0 | −1 | 0 | −1 | 2 | 2 | 1 | 4 |   |   |   |   |   |   |   |   |   |   |
| N | −4 | 0 | −1 | 1 | 0 | 0 | 2 | 1 | 2 |   |   |   |   |   |   |   |   |   |   |   |
| E | −5 | 0 | −1 | 0 | 0 | 0 | 3 | 4 |   |   |   |   |   |   |   |   |   |   |   |   |
| D | −5 | 1 | −1 | 0 | 0 | 0 | 4 |   |   |   |   |   |   |   |   |   |   |   |   |   |
| T | −2 | 0 | 0 | 1 | 1 | 3 |   |   |   |   |   |   |   |   |   |   |   |   |   |   |
| A | −2 | 1 | 1 | 1 | 2 |   |   |   |   |   |   |   |   |   |   |   |   |   |   |   |
| S | 0 | 1 | 1 | 1 |   |   |   |   |   |   |   |   |   |   |   |   |   |   |   |   |
| P | −3 | −1 | 6 |   |   |   |   |   |   |   |   |   |   |   |   |   |   |   |   |   |
| G | −3 | 5 |   |   |   |   |   |   |   |   |   |   |   |   |   |   |   |   |   |   |
| C | 12 |   |   |   |   |   |   |   |   |   |   |   |   |   |   |   |   |   |   |   |

When forming the fusion protein of the invention, it may, but not necessarily, use a linker or a connector. When a linker is present, the chemical structure of it may be flexible since it primarily functions as a spacer. Linkers may be composed of amino acids linked together by peptide bonds. In some embodiments of the invention, the linker consists of 1 to 20 amino acids linked by peptide bonds. In some embodiments, the 1 to 20 amino acids are selected from the 20 naturally occurring amino acids. In various embodiments, the 1 to 20 amino acids are selected from consists of multiple amino acids that are spatially unhindered. In other embodiments, the spatially unhindered amino acids consist of glycine and alanine. The G-rich polypeptides of the present invention may be selected from (G) 3-S, i.e., "GGGS", (G) 4-S, i.e., "GGGGS" and (G) 5-S, i.e., "GGGGGS". In some embodiments, the linker comprises GGGGSGGGGS (SEQ ID NO: 32), GGGGSGGGGSGGGGS (SEQ ID NO: 33) or GGGGSGGGGSGGGGSA (SEQ ID NO: 33). Other suitable linkers include: GGGGGSGGGGSGGGGS (SEQ ID NO: 34), GGGKGGGG (SEQ ID NO: 35), GGGNGSGG (SEQ ID NO: 36), GGGGGGGG (SEQ ID NO: 37) and GPNGG (SEQ ID NO: 38). Although a 15 amino acid residue linker was found to play a particularly good role for the dual-target fusion protein, the present invention contemplates linkers of any length or composition.

Linkers described herein are exemplary, and the linker disclosed herein may be much longer and may contain other residues. Linkers in the present invention may also be non-peptide linkers. For example, an alkyl linker can be used, such as —NH—(CH2)$_S$—C(O)—, wherein s=2-20. These alkyl linkers may be further substituted with any non-sterically hindered group including, but not limited to, lower alkyl (e.g., C1-C6), lower acyl, halogen (e.g., Cl, Br), CN, NH$_2$ or phenyl. An exemplary non-peptidic linker can also be a polyethylene glycol linker, wherein the linker has a molecular weight of 100-5000 kD, such as 100-500 kD.

As used herein, "one or more" amino acid substitutions is defined where "more" means greater than one, such as from 1 to 30, 1 to 20, 1 to 10, 1 to 5, or such as 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30.

The "first" and "second" described in this article are only for the purpose of distinguishing the description and have no special meaning.

The "ADCC effect" described herein is antibody-dependent cellular cytotoxicity (ADCC); human IgG subclasses (G1, G2, G3, G4) have different biological activities (referred to as effector functions). These effector functions are often mediated by interaction with the FcγR receptor (FcγR) or by binding to complement 1 (C1q) sub-component, wherein the complement 1 sub-component recognizes and binds to the heavy chain of immunoglobulin G or immunoglobulin M, initiating the classic complement pathway. Binding to FcγR can result in antibody-dependent cell-mediated cytolysis, whereas binding to complement factors can result in complement-mediated cytolysis, i.e., complement-dependent cytotoxicity (CDC).

As used herein, the term "comprising" usually means the recited elements but not excluding other elements.

The terms "protein" and "polypeptide" are used interchangeably and, in their broadest sense, refer to a compound of two or more subunits amino acids, amino acid analogs or peptidomimetics. Subunits can be linked by peptide bonds. In another embodiment, the subunits may be linked by other bonds, such as esters, ethers, amino groups, and the like. The protein or polypeptide must contain at least two amino acids and there is no limit to the maximum number of amino acids that can make up the protein or peptide sequence. The term "amino acid" as used herein refers to natural and/or unnatural or synthetic amino acids including D and L optical isomers of amino acids, such as glycine, D and L optical isomers, amino acid analogs and peptide mimetics.

"Homology" or "identity" or "similarity" refers to the sequence similarity between two peptides or between two nucleic acid molecules. Homology can be determined by comparing the positions in each sequence that can be aligned for comparative purposes. When the positions in the compared sequences are occupied by the same base or amino acid, these molecules are homologous at that position. The degree of homology between sequences varies with the number of matches or homologous positions shared by the sequences. An "unrelated" or "non-homologous" sequence shares less than 40% identity, or alternatively less than 25% identity with one of the sequences of the disclosure.

The term "at least 80% sequence identity" with respect to polypeptide sequence comparisons is used throughout this specification. The expression usually refers to at least 80%, at least 81%, at least 82%, at least 83%, at least 84%, at least 85%, at least 86%, at least 87%, at least 88%, at least 89%, at least 90% %, at least 91%, at least 92%, at least 93%, at least 94%, at least 95%, at least 96%, at least 97%, at least 98% or at least 99% sequence identity to each reference sequence.

When used in connection with a numerical value, the term "about" is intended to include numerical values in the range having a lower limit of 5% less than the indicated value and an upper limit of 5% greater than the indicated value.

The term "fusion protein" generally refers to a protein resulting from two or more proteins or polypeptides. A gene or nucleic acid molecule encoding two or more proteins or polypeptides can be joined to form a fusion gene or fusion nucleic acid molecule. The fusion gene or fusion nucleic acid molecule can encode the fusion protein. Translation of the fusion gene produces a single polypeptide having the property of at least one, or even each, of the two or more proteins or polypeptides prior to fusion. Recombinant fusion proteins are artificially created by recombinant DNA techniques for biological research or therapy. Recombinant fusion proteins are created by genetically engineering fusion genes. The present invention relates to recombinant fusion proteins, and the terms fusion proteins and recombinant fusion proteins are used herein with the same meaning. The fusion proteins described herein generally comprise at least two domains (A and C), and optionally a third component, a linker between the two domains. Generation of recombinant fusion proteins is known in the art and generally involves removing the stop codon from the self-encoding the cDNA sequence of the first protein or polypeptide. The cDNA sequence for the second protein is then attached in-frame by ligation or overlap extension PCR. Finally, the DNA sequence is expressed by the cell as a single protein. The protein can be engineered to include the complete sequence of two original proteins or polypeptides, or just a fraction of either.

As used in this specification and claims, the singular forms "a", "an" and "the" include plural referents unless the context clearly dictates otherwise. For example, the term "pharmaceutically acceptable carrier" includes a plurality of pharmaceutically acceptable carriers, including mixtures thereof.

"Composition" usually is a combination of two or more substances, for example, a combination of the active agent with other inert or active compounds.

"Pharmaceutical composition" usually includes the active agent in combination with an inert or active carrier, so that the composition is suitable for diagnostic or therapeutic uses, either in vivo or in vitro or ex vivo.

In the present invention, the term "therapeutically effective amount" generally refers to the minimum dose of active ingredient required to produce a therapeutic benefit in a subject. For example, for a patient exhibiting or susceptible to type 2 diabetes, obesity, or metabolic syndrome, or for preventing the onset of the disease, "therapeutically effective amount" refers to a dose that is capable of inducing, ameliorating, or causing a pathological condition, disease progression, or physiological condition that is associated with or counteracted by the disorder described above. In the present application, the term "subject" or "patient" may be human, but may also be a non-human animal, more specifically may be a companion animal such as a dog, a cat or the like, a farm animal such as a cow, a sheep, a pig, horses, or laboratory animals such as rats, mice, guinea pigs, and the like.

In the present invention, an expression of "XnY" indicates that residue X at position n in a sequence is substituted with residue Y when describing amino acid residues substitution in the sequence. For example, amino acid substitution of "R175L" indicates that residue R at position 175 in a sequence is substituted with residue L.

Fusion Protein, Preparation Method and Application

The inventors of the present invention found that known two-target fusion proteins can not completely avoid the problem of dimer dissociation. The reason may be that interactions occurring in the 3D structure of 200-amino-acid chains increase to the other end of the Fc of the double-target fusion protein; thus, more stable IgG4 Fc portion structure is required to prevent dimer dissociation.

On the basis of a large amount of inventive work by the inventors, it was surprisingly found that when two mutations (S228P and R409K) were introduced into the Fc of IgG4, the stability of the IgG4 Fc portion structure was greatly enhanced. Also, the mutated Fc had lower (or absolutely no) ADCC or CDC effects than the commonly used Fc. Therefore, the present invention provides a fusion protein structure with high stability and low ADCC/CDC effects.

In one aspect of the invention, the invention provides a fusion protein comprising or consisting of:

A-L1-B-L2-C or C-L1-B-L2-A,

Wherein A is a GLP-1 receptor agonist comprising the amino acid sequence set forth in SEQ ID NO: 1 (HGEGTFTSDV SSYLEEQAAK EFIAWLVKGG G) or at least about 80% identity to the amino acid sequence set forth in SEQ ID NO: 1, or at least about 90% identity to the amino acid sequence shown in SEQ ID NO: 1, or at least about 95% identity to the amino acid sequence set forth in SEQ ID NO: 1, or at least about 98% identity to the amino acid sequence set forth in SEQ ID NO: 1, or at least about 99% identity to the amino acid sequence set forth in SEQ ID NO: 1;

B is an IgG4-Fc mutant, comprising the amino acid sequence of SEQ ID NO: 2 (ESKYGPPCPP CPAPEAAGGP SVFLFPPKPK DTLMISRTPE VTCVVVDVSQ TKPREEQFNS TYRVVSVLTV LHQDWLNGKE EDPEVQFNWY VDGVEVHNAK YKCKVSNKGL PSSIEKTISK AKGQPREPQV YTLPPSQEEM TKNQVSLTCL VKGFYPSDIA VEWESNGQPE NNYKTTPPVL DSDGSFFLYS KLTVDKSRWQ EGNVFSCSVM HEALHNHYTQ KSLSLSLG) or at least about 95% identity to the amino acid sequence of SEQ ID NO: 2, or at least about 98% identity to the amino acid sequence set forth in SEQ ID NO: 2, or at least about 99% identity to the amino acid sequence shown in SEQ ID NO: 2, wherein, B comprises the tenth amino acid residue of P (EU number corresponding to 228) and the 191th amino acid residue of K (EU number corresponding 409);

C is FGF21, comprising the amino acid sequence set forth in SEQ ID NO: 6 (HPIPDSSPLL QFGGQVRQRY LYTDDAQQTE AHLEIREDGT VGGAADQSPE SRFLCQRPDG SLLQLKALKP GVIQILGVKT ALYGSLHFDP EACSFRERLL EDGYNVYQSE AHGLPLHLPG NKSPHRDPAP RGPARFLPLP GLPPALPEPP GILAPQPPDV GSSDPLSMVG GSQGRSPSYA S) or at least about 90% identity to the amino acid sequence set forth in SEQ ID NO: 6, or at least about 95% identity to the amino acid sequence set forth in SEQ ID NO: 6, or at least about 98% identity to the amino acid sequence set forth in SEQ ID NO: 6, or a polypeptide having at least about 99% identity to the amino acid sequence set forth in SEQ ID NO: 6 and having FGF21 activity; and L1 and/or L2 are a polypeptide comprising 5 to 50 amino acid residues and the polypeptide comprises at least 50% G.

In some embodiments, A comprises or consists of the amino acid sequence of SEQ ID NO: 7 (HX$_1$EGTFTSDVSSYLEX$_2$QAAK EFIAWLX$_3$X$_4$GX$_5$X$_6$) (SEQ ID NO: 7), Wherein, X$_1$ is selected from G or V;
X$_2$ is selected from E or G;
X$_3$ is selected from V or K;
X$_4$ is selected from K or N;
X$_5$ is selected from G or E; and
X$_6$ is selected from G or P or absent.

In other embodiments, A comprises or consists of the amino acid sequence set forth in SEQ ID NO: 1.

In some embodiments, B comprises or consists of the amino acid sequence set forth in SEQ ID NO: 8, (SEQ ID NO: 8)
ESKYGPPCPP CPAPX$_7$X$_8$X$_9$GGP SVFLFPPKPK DTLMISRTPE

VTCVVVDVSQ EDPEVQFNWY VDGVEVHNAK TKPREEQFX$_{10}$S

TYRVVSVLTV LHQDWLNGKE YKCKVSNKGL PSSIEKTISK

AKGQPREPQV YTLPPSQEEM TKNQVSLTCL VKGFYPSDIA

VEWESNGQPE NNYKTTPPVL DSDGSFFLYS KLTVDKSRWQ

EGNVFSCSVM HEALHNHYTQ KSLSLSLGX$_{11}$

Wherein, X$_7$ is selected from P or E;
X$_8$ is selected from F, V or A;
X$_9$ is selected from L, E or A;
X$_{10}$ is selected from N or A; and
X$_{11}$ is selected from K or absent.

In other embodiments, B comprises or consists of the amino acid sequence set forth in SEQ ID NO: 2.

In some embodiments, C comprises or consists of the amino acid sequence set forth in SEQ ID NO: 9, (SEQ ID NO: 9)
HPIPDSSPLL QFGGQVRQRY LYTDDAQQTE AHLEIREDGT

VGGAX$_{12}$DQSPE SLLQLKALKP GVIQILGVKT SRFLCQRPDG

ALYGSLHFDP EACSFREX$_{13}$LX$_{14}$ EDGYNVYQSE AHGLPLHX$_{15}$PG

NKSPHRDPAP RGPX$_{16}$RFLPLP GLPPALPEPX$_{17}$ X$_{18}$X$_{19}$LAPQPPDV

GSSDPLX$_{20}$MVX$_{21}$ X$_{22}$X$_{23}$QG X$_{24}$SPSX$_{25}$X$_{26}$ S

Wherein, X$_{12}$ is selected from A, K, R, E or Q;
X$_{13}$ is selected from L, D, R, E, Q, K or T;
X$_{14}$ is selected from L or K;
X$_{15}$ is selected from L or C;
X$_{16}$ is selected from A or C;
X$_{17}$ is selected from P or A;
X$_{18}$ is selected from G or A;
X$_{19}$ is selected from I or V;
X$_{20}$ is selected from S, H, C or R;
X$_{21}$ is selected from G, E, A, D or S;
X$_{22}$ is selected from P, A, E, Q, W, C, G or T;
X$_{23}$ is selected from S, L, V or M;
X$_{24}$ is selected from R, L, H or P;
X$_{25}$ is selected from Y, S, A or F; and
X$_{26}$ is selected from A, S, E or G.

In other embodiments, the C further comprises:
a) amino-terminal truncation of not more than 8 amino acid residues;
b) carboxy-terminal truncation of not more than 12 amino acid residues;
c) amino-terminal truncation of not more than 8 amino acid residues and carboxy-terminal truncation of not more than 12 amino acid residues; or
d) carboxy-terminal extension of no more than 6 amino acid residues.

In some embodiments, L1 and/or L2 comprise 1, 2 or 3 G-rich polypeptides, in some embodiments, L1 and/or L2 are selected from GGGGSGGGGS (SEQ ID NO: 32) or GGGGSGGGGSGGGGS (SEQ ID NO: 13) or GGGGSGGGGSGGGGSA (SEQ ID NO: 33).

In some embodiments, the fusion protein is homodimers.
In other embodiments, the fusion protein is non-homodimers.

The natural FGF21 molecule contains a site susceptible to protease hydrolysis; its half-life in vivo is very short. Since the three-dimensional structure of FGF21 has not been solved, researchers have made various attempts to reform its structure in anticipation of obtaining a longer half-life. These attempts include the truncation, elongation, substitution, insertion or deletion of certain amino acids on the basis of a natural amino acid sequence. Some researchers even mutate sites one by one and look forward to finding the key core that affects activity and half-life.

The present invention provides a dual-target fusion protein of GLP-1 and FGF21, which has a mutation site different from the existing published fusion protein. The inventor has unexpectedly found that the fusion protein provided herein has a longer half-life and can be administered for more than one week. Even more gratifying is that the fusion protein can exert a synergistic effect, has a remarkably stable hypoglycemic effect, and has good biological activities of lowering lipid and reducing body weight.

In another aspect of the invention, the invention provides a homodimeric fusion protein comprising or consisting of:

A-L1-B-L2-C,

Wherein, A is a GLP-1 receptor agonist comprising the amino acid sequence set forth in SEQ ID NO: 10 (HX$_1$EGTFTSDV SSYLEX$_2$QAAK EFIAWLVKGX$_5$G), wherein X$_1$ is selected from G or V; X$_2$ is selected from E or G; and X$_5$ is selected from G or E.

B is an IgG4-Fc variants comprising SEQ ID NO: 11 (ESKYGPPCPP CPAPEX$_8$X$_9$GGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS KLTVDKSRWQ EGNVFSCSVM HEALHNHYTQ KSLSLSLGX$_{11}$), wherein X$_8$ is selected from F, V or A; X$_9$ is selected from L, E or A; X$_{11}$ is selected from K or absent.

C is FGF21, comprising SEQ ID NO: 12 (HPIPDSSPLL QFGGQVRQRY LYTDDAQQTE AHLEIREDGT VGGAVDQSPE SLLQLKALKP GVIQILGVKT SRFLCQRPDG ALYGSLHFDP EACSFREX$_{13}$LL EDGYNVYQSE AHGLPLHLPG NKSPHRDPAP RGPARFLPLP GLPPALPEPP GILAPQPPDV GSSDPL X$_{20}$MVG X$_{22}$SQG X$_{24}$SPSX$_{25}$A S)

Wherein X$_{13}$ is selected from L, D, R, E;
X$_{20}$ is selected from S, H or C;
X$_{22}$ is selected from A or G;
X$_{24}$ is selected from R, L or P; and
The amino acid mutation at position X$_{25}$ is selected from any one of the following: Y, S, F.

L1 and/or L2 are a polypeptide comprising 5 to 50 amino acid residues and the polypeptide comprises at least 50% G.

In some embodiments, A comprises or consists of the amino acid sequence set forth in SEQ ID NO: 1.

In some embodiments, B comprises or consists of the amino acid sequence set forth in SEQ ID NO: 2.

In some embodiments, the homodimeric fusion protein comprises or consists of the amino acid sequence set forth in SEQ ID NO: 5, 17, 18, 19, 20, 21.

In another aspect of the invention, the invention provides polynucleotides encoding the fusion proteins of the invention. The polynucleotide encoding the above protein may be in the form of RNA, or in the form of DNA, including cDNA and synthetic DNA. The DNA may be double-stranded or single-stranded. The sequence encoding the protein of the invention may be different due to the redundancy or degeneracy of the genetic code. Polynucleotides encoding proteins of the invention may comprise the following: only proteins coding sequences, proteins coding sequences and other coding sequences such as leader or secretory sequences or preprotein sequences; proteins coding sequences and non-coding sequences such as intron or 5' and/or 3' non-coding sequences of an protein coding sequence. Thus, the term "polynucleotide encoding a protein" encompasses polynucleotides which may include not only proteins coding sequences but also other coding sequences and/or non-coding sequences.

In a further aspect of the invention, there is also provided a vector comprising a polynucleotide according to the invention. The expression vector usually replicates in the host organism either as an additional body or as an integral part of the host's chromosomal DNA. In general, expression vectors contain selection markers such as tetracycline, neomycin, and dihydrofolate reductase to allow detection of those cells transformed with the desired DNA sequence.

In a further aspect of the invention, there is also provided a host cell comprising a vector according to the invention. The dual-target protein of the present invention can easily be produced in mammalian cells such as CHO, NSO, HEK293 or COS cells, in bacterial cells such as *E. coli, Bacillus subtilis, Pseudomonas* fluorescence, or in fungal or yeast cells. Host cells (for example HEK293) are cultured using techniques known in the art.

In a further aspect of the invention, there is also provided a method of preparing a fusion protein according to the invention; the method comprises expressing a vector according to the invention in a host cell. The vector containing the polynucleotide sequence of interest (eg, the dual-target fusion protein and the expression control sequence) can be transferred to the host cell by well-known methods, and such methods vary depending on the type of host cell. For example, calcium chloride transformation is commonly used for prokaryotic cells, whereas calcium phosphate treatment or electroporation can be used for other host cells.

In another aspect of the present invention, there is also provided use of the fusion protein of the present invention in the manufacture of a pharmaceutical composition, the pharmaceutical composition comprises a fusion protein of the invention, and at least one pharmaceutically acceptable carrier, diluent or excipient. In some embodiments, the medicament is used for the treatment of metabolic diseases. In some embodiments, the metabolic disease is diabetes, such as type 2 diabetes. In other embodiments, the metabolic disease is obesity. Other embodiments include metabolic disorders such as dyslipidemia, hypertension, hepatic steatosis (for example non-alcoholic fatty liver (NASH)), cardiovascular diseases (for example atherosclerosis and aging).

EXAMPLE

The disclosure is further understood by the following examples, which are merely examples of the disclosure. The present disclosure is not to be limited in scope by the illustrated embodiments, which are merely intended to illustrate a single aspect of the present invention. Any method that is functionally equivalent is included in the scope of the present invention. From the above description and the drawings, various modifications of the invention in addition to those described herein will be apparent to those skilled in the art. These modifications are also within the scope of the claims.

Example 1: Construction of Vector

The fusion protein carrier was constructed by using a molecular cloning method, the mutants and sequences of the fusion proteins were shown in Table 1.

TABLE 1

| Fusion protein | GLP-1 portion | Fc portion | FGF21 portion | SEQ ID NO: |
|---|---|---|---|---|
| Dulaglutide | A8G\G22E\R36G | S228P\F234A\L235A | non | 3 |
| S1F1 | non | S228P\F234A\L235A\R409K | L98R\P171G | 4 |
| D1F1 | A8G\G22E\R36G | S228P\F234A\L235A\R409K | L98R\P171G | 5 |
| D1F2 | A8G\G22E\R36G | S228P\F234A\L235A | L98R\P171G | 16 |

TABLE 1-continued

| Fusion protein | GLP-1 portion | Fc portion | FGF21 portion | SEQ ID NO: |
|---|---|---|---|---|
| D2F1 | A8G\G22E\R36G | 8228P\F234A\L235A\R409K | L98R\P171G\Y179F | 17 |
| D3F1 | A8G\G22E\R36G | 8228P\F234A\L235A\R409K | L98R\S167H\P171A | 18 |
| D4F1 | A8G\G22E\R36G | 8228P\F234A\L235A\R409K | L98R\S167H\P171A\R175L | 19 |
| D5F1 | A8G\G22E\R36G | 8228P\F234A\L235A\R409K | L98R\S167H\P171A\R175L | 20 |
| D6F1 | A8G\G22E\R36G | 8228P\F234A\L235A\R409K | L98R\G170E\P171A\S172L | 21 |
| D7F1 | A8G\G22E\R36G | 8228P\F234A\L235A\R409K | wild type | 22 |

The nucleotide sequence encoding dulaglutide and the SIF1 fusion protein was synthesized by Kingsbury Biotechnology Co., Ltd. through chemical methods. The nucleotide sequence encoding DIF1 fusion protein was obtained by connecting fragments of nucleotide sequences respectively encoding GLP-1 and Fc-FGF21 by SOE-PCR technique, the nucleotide sequences respectively encoding GLP-1 and Fc-FGF21 were obtained by PCR through designing a primer and using dulaglutide and S1F1 fusion protein nucleotide sequences as templates.

The nucleotide sequences encoding D1F2, D2F1, D3F1, D4F1, D5F1, D6F1 and D7F1 fusion proteins were synthesized by Suzhou Genewiz Biological Technology Co., Ltd through chemical methods.

The nucleotide sequence and the vector plasmid pcDNA3.4 were digested with endonucleases HindIII and EcoRI (TAKARA, Japan) at 37° C. The digested products were recovered by purification using the Gel Extraction Kit (OMEGA, America) according to the manufacturer's instructions. The purified target gene was ligated with the vector using a DNA Ligation Kit Ver.2.1 (TAKARA, Japan) according to the manufacturer's instructions and incubated at 16° C. for 1 hour to obtain a recombinant expression plasmid.

The above recombinant plasmid was transformed into competent DH5a cells. Bacteria was coated into an ampicillin plate. The monoclonal on the plate was picked and cultured in 1 ml of LB medium (peptone 10 g/L, yeast extract 5 g/L, sodium chloride 10 g/L and agar 2%, antibiotic content 100 g/mL) to extract the plasmid. After sequencing and validation, a series of validated correct expression vectors were extracted with Invitrogen Plasmid Kit and digested with restriction enzyme PvuI (TAKARA, Japan). After linearization, the product was purified by ethanol precipitation method and stored at −20° C. for future use.

Example 2: Transfection of Encoding Dulaglutide Vector and Expression in Cells After CHOKISV GS-KO (Lonza) host cells were resuscitated with CD CHO medium (gibco), cells were collected and transfected at a cell density of about $8 \times 10^5$ cells/mL. The cells were transfected with about $1 \times 10^7$ cells and the vector was about 40 μg and transfected by means of electric shock (Bio-Rad, Gene PulS Xcell). After shock, the cells were cultured in 20 mL of CD CHO medium. On the second day of culture, the cells were collected by centrifugation at 200 g for 10 min. The cells were resuspended and cultured in 20 mL of CD CHO medium with a final concentration of 50 μM obtained by addition of MSX (sigma). When the cell density was about $0.6 \times 10^6$ cells/mL, the obtained mixed clone was passaged with CD CHO medium and the passage cell density was about $0.2 \times 10^6$ cells/mL. When the cell viability was about 90%, the cell culture fluid was collected.

Example 3: Transfection of S1F1 and D1F1, D1F2, D2F1, D3F1, D4F1, D5F1, D6F1, D7F1 Fusion Protein Vectors and Expression in Cells After HEK293F host cells (Invitrogen, Freestyle 293F) were resuscitated with 293 Expression Medium (Invitrogen), they were collected and transfected at a cell density of about $1 \times 10^6$ cells/mL. The cells were transfected with FreeStyle™ MAX Reagent Transfection Kit. There were about $3 \times 10^7$ cells and the vector was about 37.5 μg. After transfection, the cells were cultured in 30 mL of 293 Expression Medium. On the second day of culture, genetic transformants started to screen with geneticin (merck). As needed due to cell growth, medium was replaced every 3 to 5 days for screening. After about 14 days of selection, resistant clones appeared and could be expanded. The cell passage density was about $0.5 \times 10^6$ cells/mL. The obtained mixed clone was subcultured with 293 Expression Medium. When the cell viability was about 90%, the cell culture fluid was collected.

Example 4: Purification of Protein from the Collected Cell Fermentation Broth The translation level of the eight fusion proteins described in Examples 2 and 3 were detected. The collected cell culture medium was purified by Protein A chromatography (EzFast Protein A Diamond, Bestchrom). The equilibration solution was 20 mM PBS, 0.15 M NaCl, pH 7.4. The fusion protein dulaglutide and the SIF1 were eluted with 0.1 M citric acid buffer, pH 3.2±0.2. D1F1, D1F2, D2F1, D3F1, D4F1, D5F1, D6F1 and D7F1 fusion proteins were eluted with 0.1 M glycine pH 3.2±0.2. The target eluate was collected at target absorption peak and dialyzed with PBS buffer to take part of the sample for mass spectrometry. Mass spectrometry detection molecular weight was consistent with theoretical molecular weight, and they were in homodimeric form. The fusion protein was confirmed to be the target fusion protein. At the same time, the collected samples were detected by 10% SDS-PAGE electrophoresis after reduction and non-reduction. Electrophoresis showed a single band having a band size consistent with theory.

Figure 2:
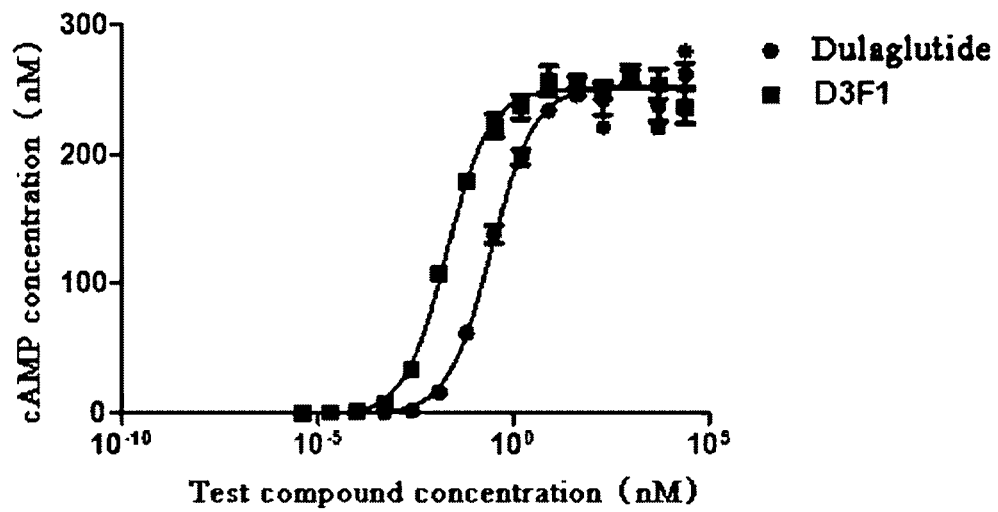
FIG. 2 shows plots of cAMP concentration as a function of dulaglutide or D3F1 detected by using a GLP-1R cell model.

Example 5: Detection of cAMP Produced by Fusion Protein Stimulation in HEK293/GLP-1R/KLB Cell Model cAMP was produced by HEK293 cells with GLP-1R/KLBGLP-1 expression stimulated by the test fusion protein. The CAMP assay kit (Cisbio 62AM6PEC) was used to measure the concentration of the fusion protein and the amount of cAMP produced by stimulation to establish a dose-response curve measuring the activity of the test compounds in vitro. Two fusion proteins were tested, including the dulaglutide and D3F1 fusion protein groups. CAMP test results are shown in FIG. 2 and Table 2.

TABLE 2

| The test protein | Dulaglutide | D3F1 |
|---|---|---|
| EC50 | 0.2683 | 0.01984 |
| Amino acid sequence | SEQ ID NO: 3 | SEQ ID NO: 18 |

Example 6: Investigation of the Effect of Mutation of Fc409 from R to K on the Stability of the Fusion Protein by Microcalorimetric Differential Scanning Calorimetry (DSC)

Figure 3:
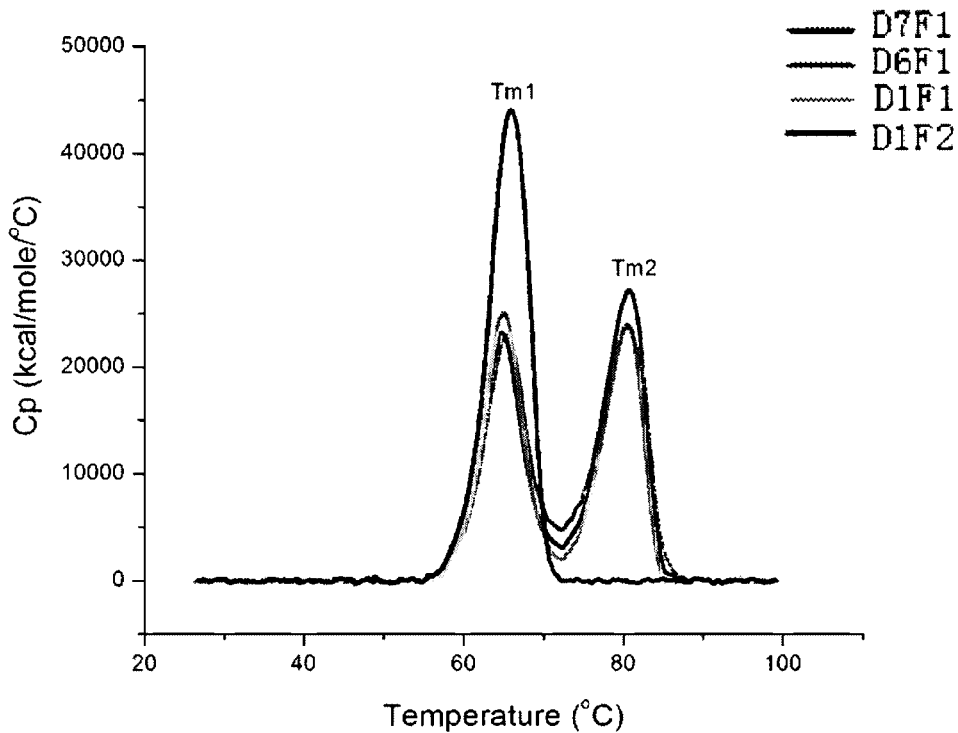
FIG. 3 shows microcalorimetric differential scanning calorimetry curves of fusion proteins D1F1, D1F2, D6F1 and D7F1.

The fusion proteins D1F1, D1F2, D6F1 and D7F1 obtained in Example 4 were each diluted to 1 mg/ml with a blank buffer system (20 mM PBS pH 7.4), taking 500 μL for DSC (Microcal vp-Capillary DSC) analysis. The scanning temperature was from 20° ° C. to 100° C. and the heating rate was 1 °C/min. The microcalorimetric scanning calorimetry results are shown in FIG. 3, and the obtained Tm values after fitting with Origin™ are shown in Table 3.

TABLE 3

| Test protein | Protein concentration (nM) | DH (enthalpy) | Tm1 (° C.) | Tm2 (° C.) |
|---|---|---|---|---|
| D7F1 | About 9.7 | 3.56E+08 | 65.43 | 80.74 |
| D6F1 | | 3.28E+08 | 64.73 | 80.7 |
| D1F1 | | 3.12E+08 | 64.93 | 80.58 |
| D1F2 | | 2.85E+08 | 65.71 | N/A |

The higher the phase transition temperature Tm, the stronger the molecular stability. It can be seen from the above results that the Tm1 and Tm2 values of the samples D7F1, D6F1 and D1F1 are basically the same, indicating that the stability of the three proteins is more consistent. The Tm1 value of D1F2 is basically the same as that of the other three samples, but its Tm2 is significantly lower Tm2 values for other samples. From the structural analysis of the D1F1 and D1F2 proteins, it can be concluded that the main difference is that the R at amino acid 409 in CH3 domain of IgG4 Fc is mutated to K, and this mutation resulted in a significantly higher Tm2 for D1F1 than the Tm2 value for D1F2. The results showed that the mutation from R to K at position 409 in the CH3 domain of IgG4 Fc in DIF1 increased the Tm value of the domain and thus enhanced its protein stability.

Example 7: A Study of the Effect of Fc409 Mutation from R to K on the Hypoglycemic Effect of the Fusion Protein The efficacy of the fusion protein in the db/db mouse model (Institute of Model Animal Science, Nanjing University) was studied. The mice were randomly divided into three groups, including blank group, D1F1 group and D1F2 group. Each db/db mouse was injected with 24.5 nM/kg fusion protein, the administration volume was 10 ml/kg. Seven mice were used per fusion protein and administrated by once injection, and the blood glucose level was measured at different times. The results are shown in Table 4. As a result, the 409th of IgG4 Fc was mutated to K, hypoglycemic effect could maintain longer.

TABLE 4

| | blood glucose concentration (mmol/L) | | | |
|---|---|---|---|---|
| Group | Day 0 | Day 2 | Day5 | Day 8 |
| Blank group | 24.0 ± 5.1 | 21.0 ± 6.5 | 23.8 ± 6.1 | 19.8 ± 5.4 |
| D1F1 | 24.0 ± 5.2 | 8.7 ± 2.5 | 15.2 ± 4.5 | 16.5 ± 5.2 |
| D1F2 | 24.5 ± 4.3 | 8.4 ± 2.5 | 17.3 ± 5.5 | 19.5 ± 3.7 |

Figure 4:
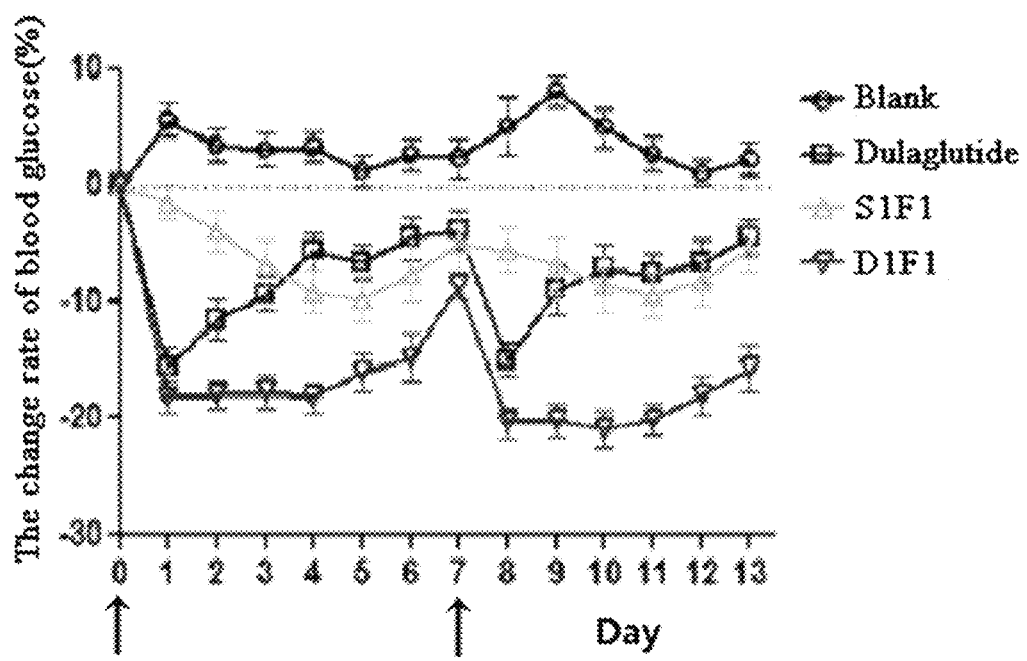
FIG. 4 shows the blood glucose levels after administration of dulaglutide, S1F1 and D1F1 in db/db mouse model.

Example 8: A Study of the Hypoglycemic Effect of Dulaglutide, S1F1, D1F1 in db/db Mouse Model Efficacy of fusion proteins in db/db mouse model (Institute of Model Animal Science, Nanjing University) was studied. A series of purified fusion proteins were diluted with 10 mM PBS during the experiment. The mice were randomly divided into four groups, including blank group, dulaglutide group, S1F1 group and D1F1 group. Each db/db mouse was injected with 40 nM/kg fusion protein, the administration volume was 3 ml/kg, and 10 mice per fusion protein were injected once a week for two weeks. The results of sampling changes in blood glucose after administration are shown in FIG. 4. The DIF1 group had a significant hypoglycemic advantage and its hypoglycemic curve was more stable than both the dulaglutide and S1F1 groups.

Figure 5:
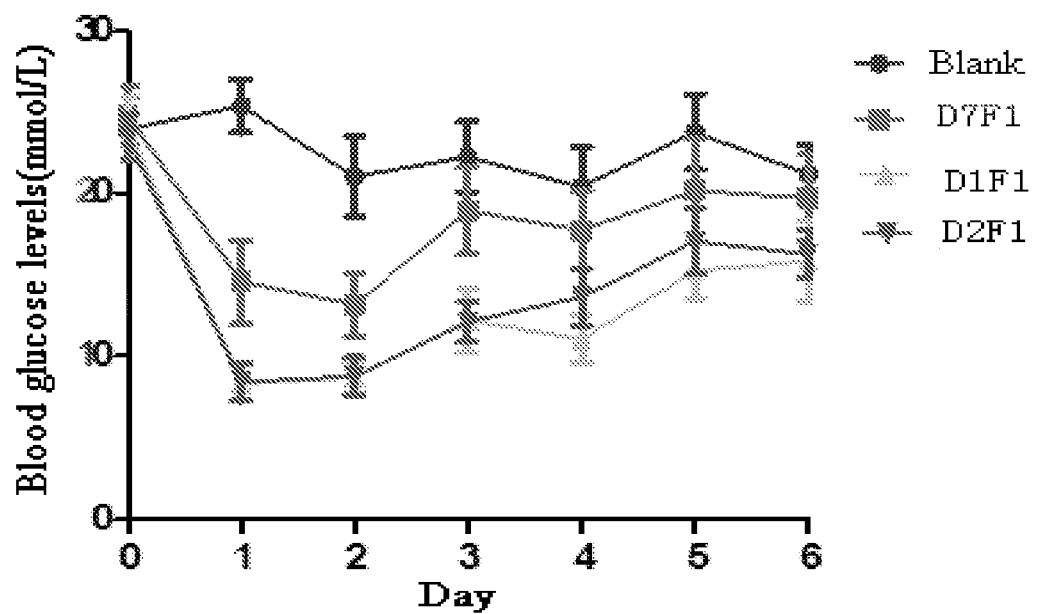
FIG. 5 shows the blood glucose levels after administration of fusion proteins D1F1, D2F1 and D7F1 in db/db mouse mode.

Example 9: A Study of the Hypoglycemic Effect of D1F1, D2F1, D7F1 in db/db Mouse Model The efficacy of the fusion protein in the db/db mouse model (Institute of Model Animal Science, Nanjing University) was studied. The mice were randomly divided into four groups, including blank group (10 mM PBS), D1F1 group, D2F1 group and D7F1 group. Each db/db mouse was injected with 24.5 nM/kg fusion protein (Diluted with 10 mM PBS), the administration volume was 10 ml/kg. Seven mice per fusion protein were injected once, and the blood glucose level was measured at different times. The results are displayed in FIG. 5. They showed that D1F1 and D2F1 had better hypoglycemic effects than D7F1.

Figure 6:
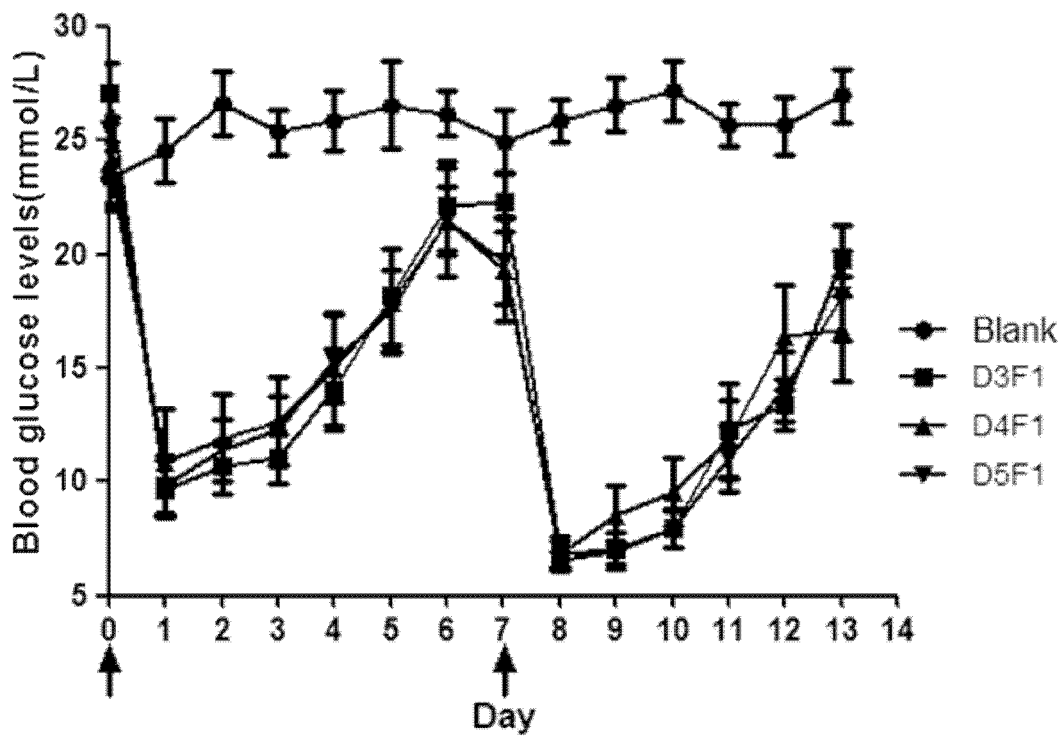
FIG. 6 shows the hypoglycemic effects after administration of fusion proteins D3F1, D4F1 and D5F1 in db/db mouse model.

Example 10: A Study of the Hypoglycemic Effect of D3F1, D4F1, D5F1 in db/db Mouse Model The efficacy of fusion proteins in db/db mouse model (Institute of Model Animal Science, Nanjing University) was studied. A series of purified fusion proteins were diluted with 10 mM PBS during the experiment. The mice were randomly divided into four groups, including blank group (10 mM PBS), D3F1 group, D4F1 group and D5F1 group. Each db/db mouse was injected with 30 nM/kg fusion protein (Diluted with 10 mM PBS), the administration volume was 10 ml/kg, and 9 mice per fusion protein were injected once a week for two weeks. The results of sampling changes in blood glucose after administration are shown in FIG. 6. D3F1, D4F1 and D5F1 showed better hypoglycemic effects.

Figure 7:
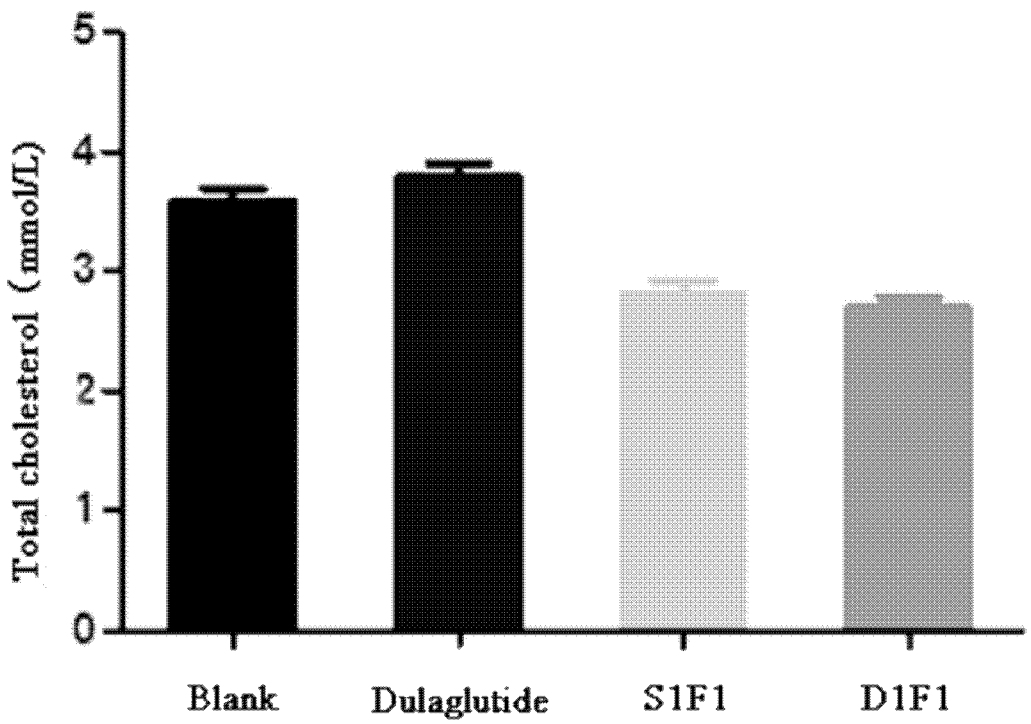
FIG. 7 shows the reduced total cholesterol effects after administration of dulaglutide, S1F1 and D1F1 in db/db mouse model.
Figure 8:
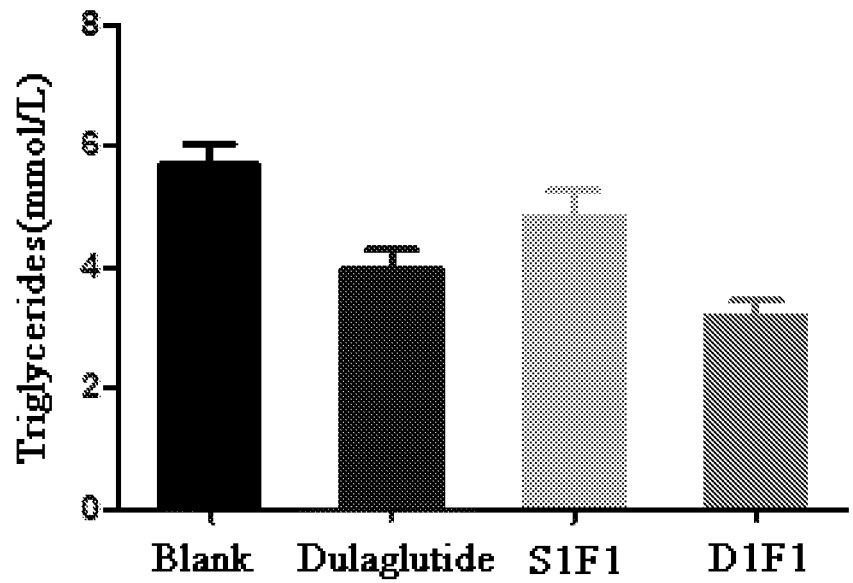
FIG. 8 shows the reduced triglyceride effects after administration of dulaglutide, S1F1 and D1F1 in db/db mouse model.

Example 11: Study on the Lipid-Lowering Efficacy Effect of Dulaglutide, S1F1, D1F1 in db/db Mouse Model The db/db model mice (Institute of Model Animal Science, Nanjing University) were randomly divided into 4 groups, including blank group (10 mM PBS), dulaglutide group, SIF1 group and DIF1 group. Each db/db mouse was injected with 40 nM/kg fusion protein (Diluted with 10 mM PBS), the administration volume was 3 ml/kg, and 10 mice per fusion protein were injected once a week for two weeks. All mice were sacrificed 14 days after the initial administration, and their blood total cholesterol (TCHO) (see FIG. 7) and triglyceride (TG) content (see FIG. 8) were measured. The ability of D1F1 to lower total cholesterol and triglyceride content was higher than that of S1F1 group and dulaglutide group.

Figure 9:
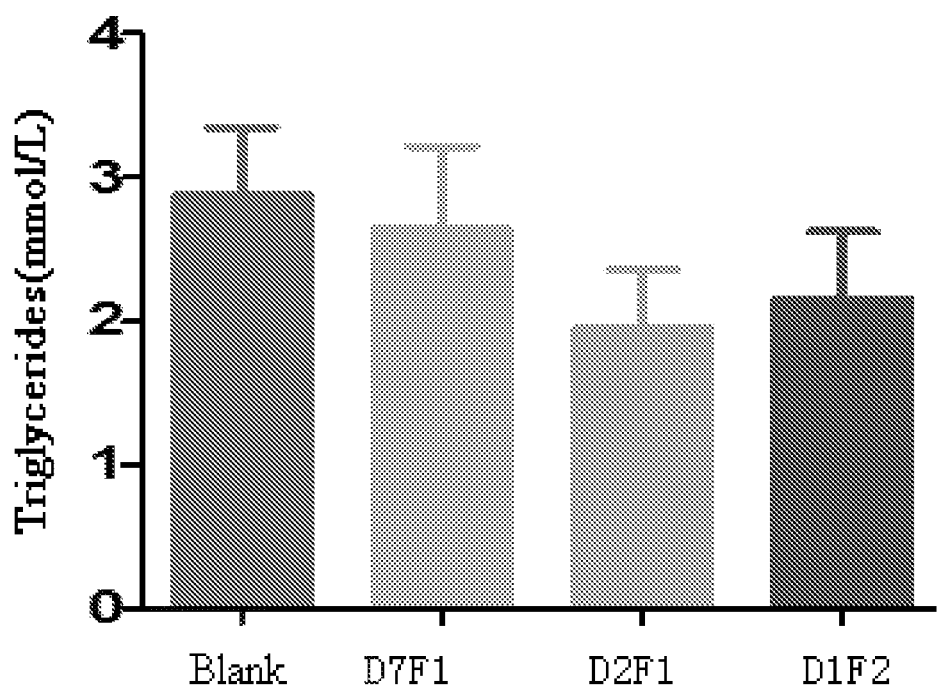
FIG. 9 shows the reduced triglyceride effects after administration of fusion proteins D1F2, D2F1 and D7F1 in db/db mouse model.
Figure 10:
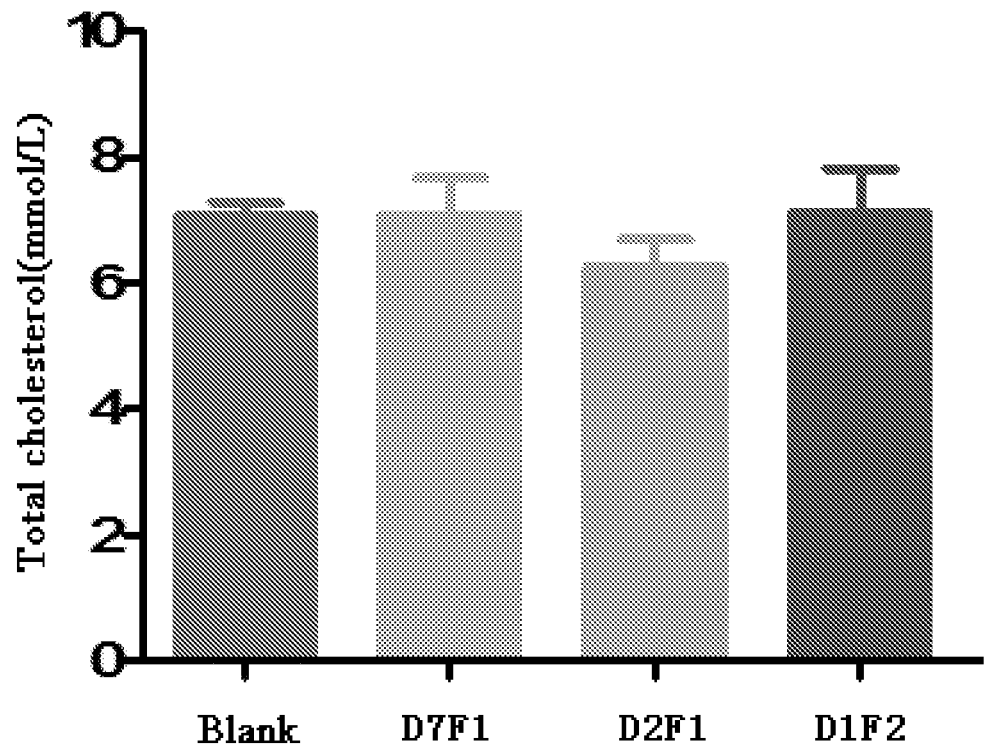
FIG. 10 shows the reduced total cholesterol effects after administration of fusion proteins D1F2, D2F1 and D7F1 in db/db mouse model.
Figure 11:
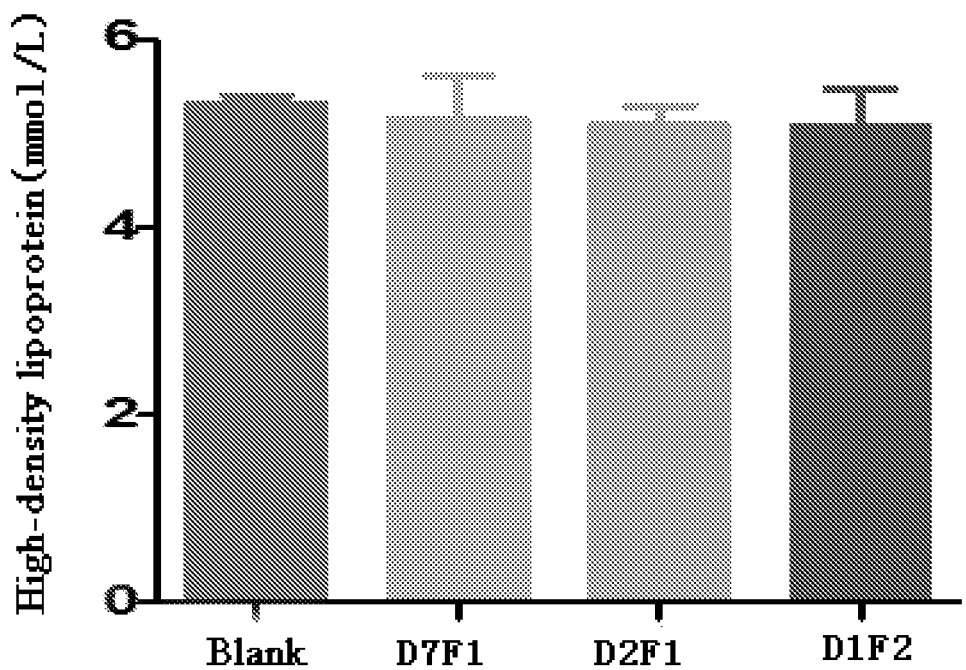
FIG. 11 shows the reduced high density lipoprotein effects after administration of fusion proteins D1F1, D2F1 and D7F1 in db/db mouse model.
Figure 12:
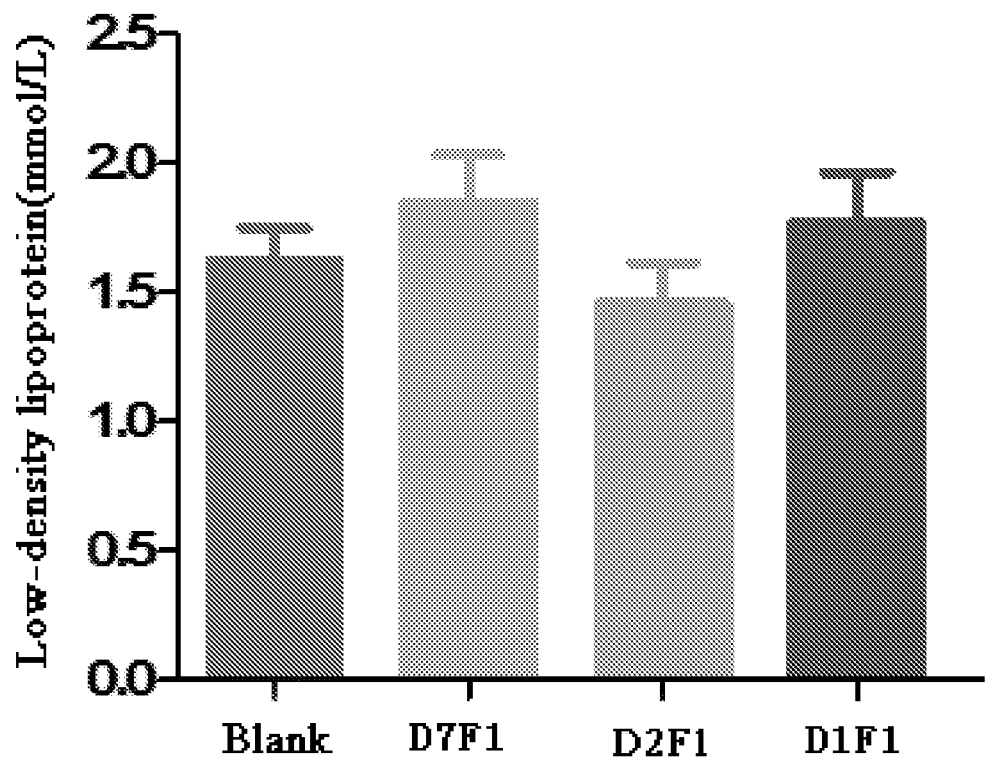
FIG. 12 shows the reduced low density lipoprotein effects after administration of fusion proteins D1F1, D2F1 and D7F1 in db/db mouse model.

Example 12: A Study of the Lipid-Lowering Efficacy of D1F2, D2F1 and D7F1 in db/db Mouse Model The db/db model mice (Institute of Model Animal Science, Nanjing University) were randomly divided into 4 groups, including blank group (10 mM PBS), D1F2 group, D2F1 group and D7F1 group. Each db/db mouse was injected with 24.5 nM/kg fusion protein (Diluted with 10 mM PBS), the administration volume was 10 ml/kg. Seven mice per fusion protein were injected once. The results of a serum triglyceride (TG) test after a single administration for 14 days are shown in FIG. 9; results of the total cholesterol (TC) content are shown in FIG. 1; results of high density lipoprotein (HDL-C) content are shown in FIG. 1, and results of the low density lipoprotein (LDL-C) content are shown in FIG. 12. The D1F2 and D2F1 groups showed a greater ability to lower triglycerides than D7F1 with a native FGF21 sequence. D2F1 showed stronger ability to lower triglyceride and total cholesterol than D1F2, which did not mutate at position 409 of IgG4 Fc.

Figure 13:
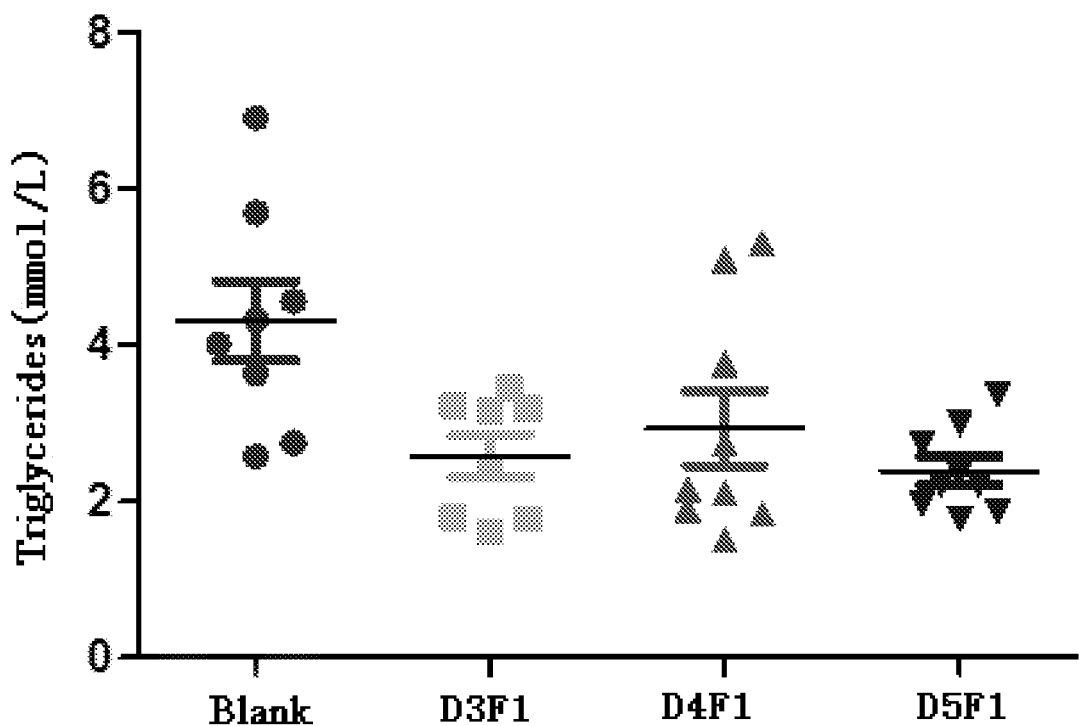
FIG. 13 shows the reduced triglyceride effects after administration of fusion proteins D3F1, D4F1, D5F1 in db/db mouse model.
Figure 14:
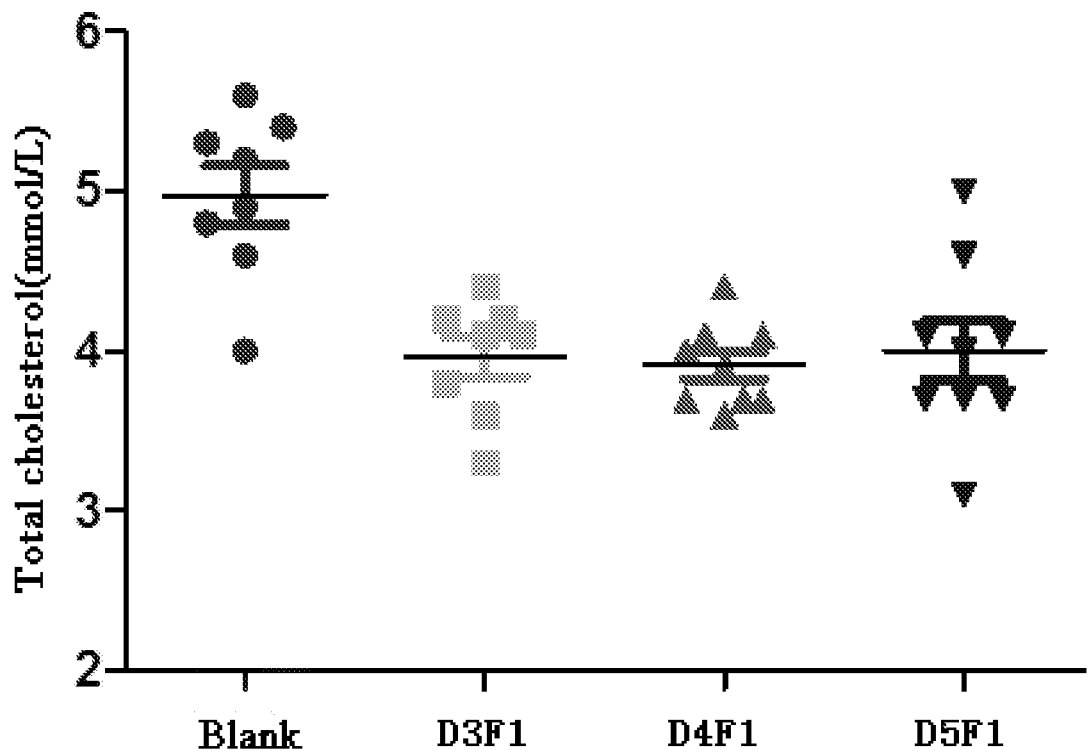
FIG. 14 shows the reduced total cholesterol effects after administration of fusion proteins D3F1, D4F1 and D5F1 in db/db mouse model.
Figure 15:
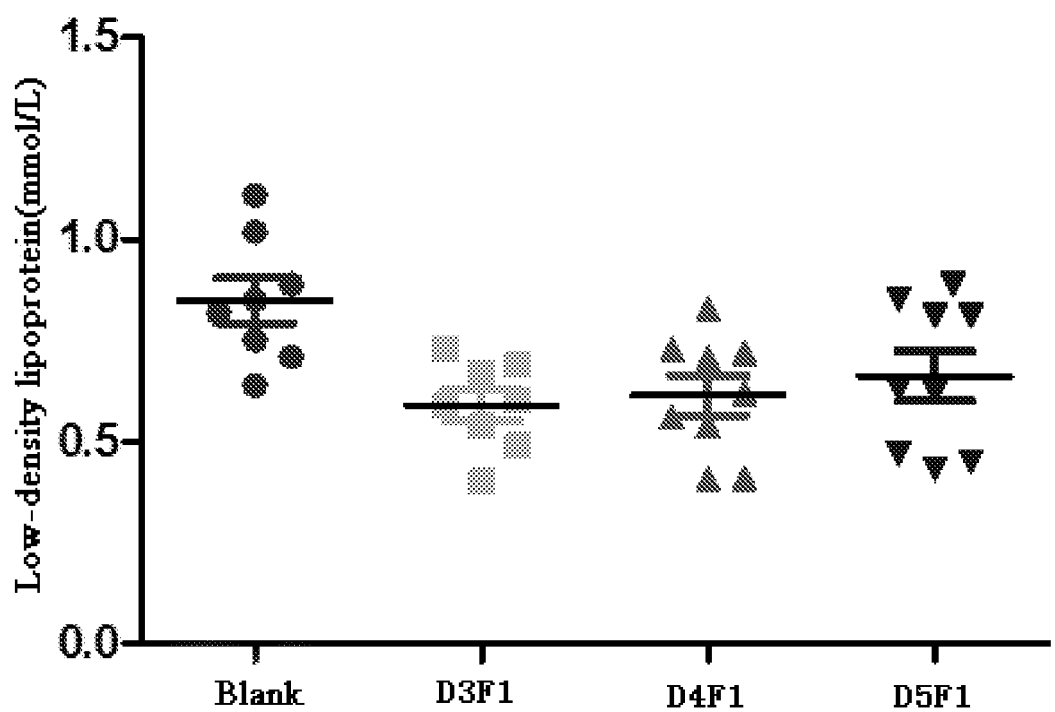
FIG. 15 shows the reduced low density lipoprotein effects after administration of fusion proteins D3F1, D4F1 and D5F1 in db/db mouse model.

Example 13: A Study of Lipid-Lowering Efficacy of D3F1, D4F1, D5F1 in db/db Mouse Model The db/db model mice (Institute of Model Animal Science, Nanjing University) were randomly divided into 4 groups, including blank group (10 mM PBS), D3F1 group, D4F1 group and D5F1 group. Each db/db mouse was injected with 30 nM/kg fusion protein (Diluted with 10 mM PBS), the administration volume was 3 ml/kg, and 9 mice per fusion protein were injected once a week for two weeks. Serum triglyceride (TG) results after 14 days of first administration are shown in FIG. 13. The total cholesterol (TCHO) results are shown in FIG. 14. Low-density lipoprotein (LDL-C) results are shown in FIG. 15.

Figure 16:
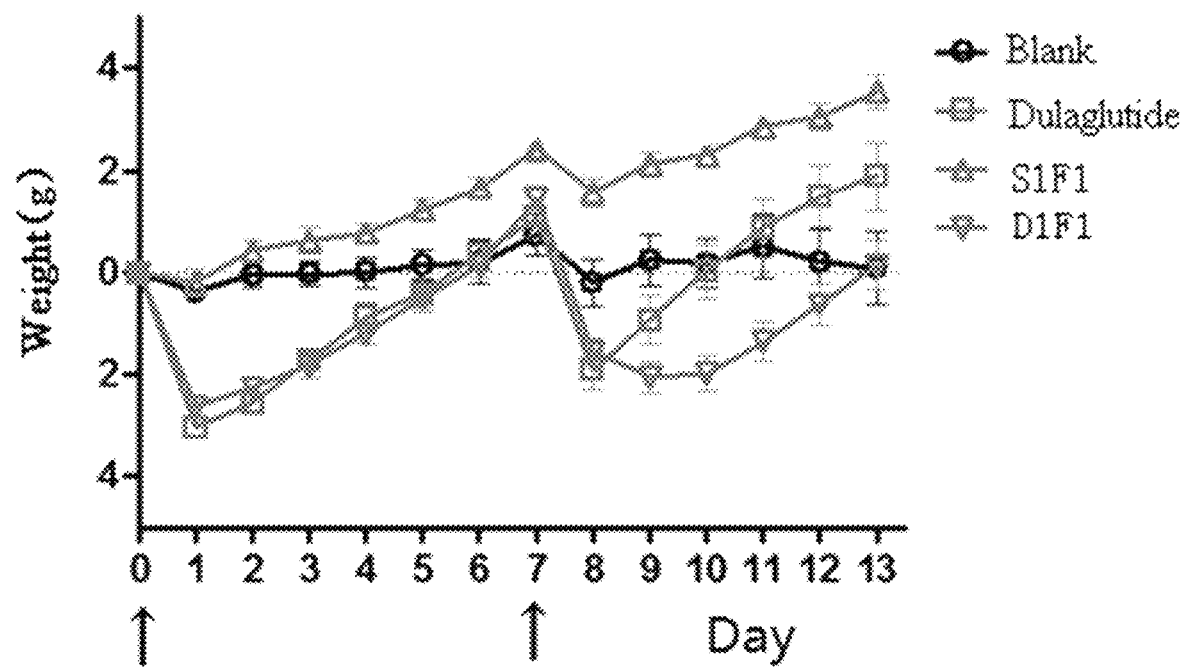
FIG. 16 shows the reduced the weight effects after administration of dulaglutide, S1F1 and D1F1 in db/db mouse model.

Example 14: A Study of the Weight-Loss Efficacy of Dulaglutide, S1F1, D1F1 in db/db Mouse Model The db/db model mice (Institute of Model Animal Science, Nanjing University) were randomly divided into 4 groups, including blank group (10 mM PBS), dulaglutide group, S1F1 group and D1F1 group. Each db/db mouse was injected with 40 nM/kg fusion protein (Diluted with 10 mM PBS), the administration volume was 3 ml/kg, and 10 mice per fusion protein were injected once a week for two weeks. Body weight was recorded daily after administration, and results are shown in FIG. 16.

Example 15: Study on the Pharmacokinetic of Dulaglutide, D1F1

Male ICR mice (Hunan Si Lake) were divided into 2 groups, each group with 3 mice, and each was subcutaneously injected with 10 nmol/kg dulaglutide or 10 nmol/kg D1F1 (Diluted with 10 mM PBS). Venous blood was collected through retro-orbital venous plexus at 1, 5, 7, 24, 48, 96, 144, 192, 240, 288 h before administration and after administration respectively. The anti-GLP-1 antibody (Bioporto, CAT. NO. ABS 033-10) was used as the capture antibody, the anti-human IgG Fc antibody (Southern Biotech, CAT. NO. 9200-05) was used as the detection antibody, the pharmacokinetic parameters were determined by the ELISA method. The results are shown in Table 5.

TABLE 5

| Test substance | Tmax (h) | Cmax (ng/ml) | AUClast (h * µg/ml) | MRTlast (h) |
|---|---|---|---|---|
| D1F1 | 6.33 | 3.77 | 149.6 | 32.47 |
| Dulaglutide | 5.67 | 1.72 | 46.9 | 37.56 |

The average plasma exposure ($AUC_{last}$) and Cmax of D1F1 fusion protein were significantly higher than those of dulaglutide, indicating that absorption of the fusion protein can be increased after fusion with FGF21. MRTlast indicates the average retention time of drug molecules in the body, which were equivalent for both D1F1 and dulaglutide in mice.

Figure 17:
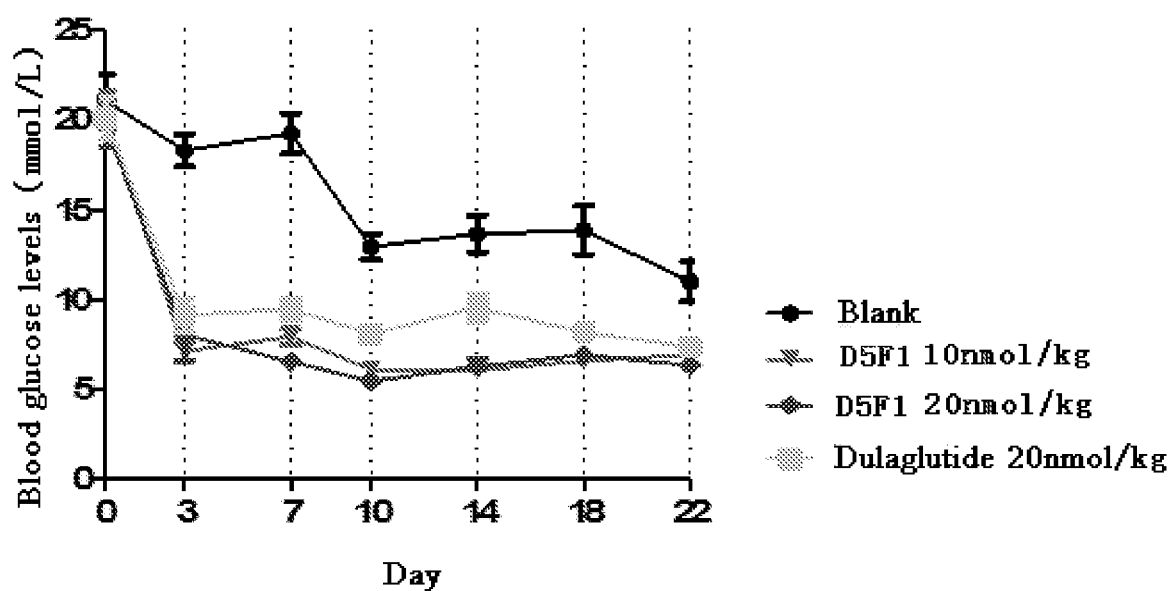
FIG. 17 shows the hypoglycemic effects after administration of dulaglutide and D5F1 in ob/ob mouse model.
Figure 18:
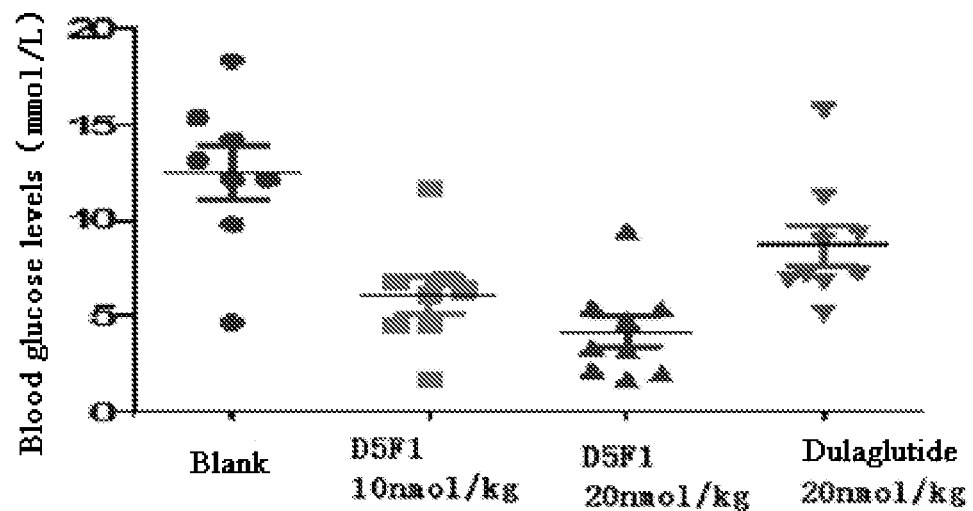
FIG. 18 shows the blood glucose concentration after administration of dulaglutide and D5F1 after 16 hours of fasting in the ob/ob mouse model.
Figure 19:
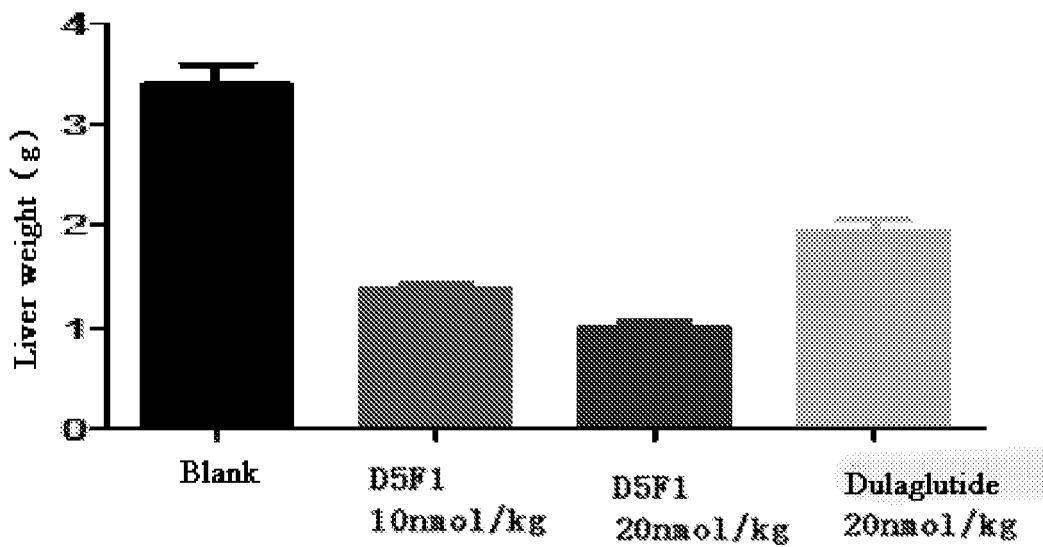
FIG. 19 shows the improving hepatic steatosis effects after administration of dulaglutide and D5F1 in the ob/ob mouse model.

Example 16: A Study of the Pharmacokinetic of Dulaglutide, D5F1 in Ob/Ob Mouse Model The ob/ob mice (Institute of Model Animal Science, Nanjing University) were randomly divided into 4 groups, including blank group (10 mM PBS), the D5F1 10 nmol/kg group, D5F1 20 nmol/kg group and dulaglutide 20 nmol/kg group (Diluted with 10 mM PBS). The administration volume was 3 ml/kg, and 9 mice per fusion protein were injected, twice a week for 3 consecutive weeks. The results of samples blood glucose testing before each administration are shown in FIG. 17. Compared with dulaglutide, D5F1 displayed a better hypoglycemic effect, and the hypoglycemic curve of the D5F1 group was more stable. Blood was taken from the orbit of the second day after the last administration for 16 hours, then serum was collected. Serum glucose was monitored (results shown in FIG. 18). After dissected, the liver was weighed (results shown FIG. 19). According to the results of liver weight, D5F1 group has better improvement on hepatic steatosis.

What is claimed is:

1. A fusion protein comprising or consisting of:
   a) a first polypeptide, wherein the first polypeptide is glucagon-like peptide-1 (GLP-1) or an analogue thereof;
   b) a second polypeptide, wherein the second polypeptide is an IgG4 Fc portion comprising the amino acid sequence of SEQ ID NO: 2, or a variant thereof; and
   c) a third polypeptide, wherein the third polypeptide is fibroblast growth factor 21 (FGF21) comprises the amino acid sequence of SEQ ID NO: 6 or a variant thereof,
   wherein the first polypeptide is linked to the second polypeptide via a first linker and the third polypeptide is linked to the second polypeptide via a second linker; and
   wherein the variant of SEQ ID NO: 2 further comprises any one or more mutations selected from E233P and N297A, as compared to the wild-type IgG4 Fc; and
   wherein the variant of SEQ ID NO: 6 further comprises one or more mutations at one or more sites selected from the group consisting of 167, 175 and 179; wherein the amino acid mutation at position 167 is selected from the group consisting of S167H and S167C; wherein the amino acid mutation at position 175 is selected from the group consisting of R175L, R175H and R175P; and wherein the amino acid mutation at position 179 is selected from the group consisting of Y179S and Y179F.

2. The fusion protein of claim 1, wherein the GLP-1 analogue comprises or consists of the amino acid sequence of SEQ ID NO: 7 (HX$_1$EGTFTSDVSSYLEX$_2$QAAKEFIAWLX$_3$X$_4$GX$_5$X$_6$),
   wherein X$_1$ is selected from G or V;
   X$_2$ is selected from E or G;
   X$_3$ is selected from V or K;
   X$_4$ is selected from K or N;
   X$_5$ is selected from G or E; and
   X$_6$ is selected from G, P or absent.

3. The fusion protein of claim 1, wherein the GLP-1 analogue comprises or consists of the amino acid sequence of SEQ ID NO: 1.

4. The fusion protein of claim 1, wherein the FGF21 variant further comprises at least one amino acid mutation at position 170 or 172, wherein
   the amino acid mutation at position 170 is selected from the group consisting of G170E, G170A, G170C, G170D, G170N, and G170S; and
   the amino acid mutation at position 172 is selected from the group consisting of S172L, S172I, S172V, S172A, and S172M.

5. The fusion protein of claim 4, wherein the FGF21 variant comprises at least one amino acid mutation at position 170 or 172, wherein
   the amino acid mutation at position 170 is selected from the group consisting of G170E, G170A, G170D, and G170S; and the amino acid mutation at position 172 is selected from the group consisting of S172L, S172V, and S172M.

6. The fusion protein of claim 4, wherein the FGF21 variant comprises at least one amino acid mutation at position 170 or 172, wherein
   the amino acid mutation at position 170 is selected from the group consisting of G170E, and G170A; and
   the amino acid mutation at position 172 is S172L.

7. The fusion protein of claim 1, wherein the FGF21 variant further comprises one or more mutations at one or more sites selected from the group consisting of 45, 100, 150, 151, 152, and 180; wherein
   the amino acid mutation at position 45 is selected from the group consisting of A45K, A45R, A45E, and A45Q;
   the amino acid mutation at position 100 is L100K;
   the amino acid mutation at position 150 is P150A;
   the amino acid mutation at position 151 is G151A;
   the amino acid mutation at position 152 is I152V; and
   the amino acid mutation at position 180 is selected from the group consisting of A180S, A180E, and A180G.

8. The fusion protein of claim 1, wherein the FGF21 variant further comprises one or more mutations at one or more sites selected the group consisting of 45 and 180,
   wherein the amino acid mutation at position 45 is selected from the group consisting of A45K, A45R, A45E, and A45Q; and the amino acid mutation at position 180 is selected from the group consisting of A180S, A180E, and A180G.

9. The fusion protein of claim 1, wherein the amino acid mutation at position 167 of the FGF21 variant is S167H; the amino acid mutation at position 175 of the FGF21 variant is R175L; and the amino acid mutation at position 179 of the FGF21 variant is Y179F.

10. The fusion protein of claim 1, wherein the first linker and the second linker each independently comprises a polypeptide of 5 to 50 amino acid residues, and the polypeptide comprises at least 50% G.

11. The fusion protein of claim 10, wherein the first linker and the second linker each independently comprises a G-rich polypeptide comprising at least 50% G.

12. The fusion protein of claim 10, wherein the first linker and the second linker each independently is selected from the amino acid sequence of SEQ ID NO: 32 (GGGGSGGGGS), or SEQ ID NO: 13 (GGGGSGGGGSGGGGS), or SEQ ID NO: 33 (GGGGSGGGGSGGGGSA).

13. The fusion protein of claim 1, wherein the fusion protein is a homodimeric fusion protein or a non-homodimeric fusion protein.

14. A pharmaceutical composition comprising the fusion protein of claim 1, and optionally one or more pharmaceutically acceptable adjuvants.

15. A method of treating a metabolic disease in a patient comprising administrating a therapeutically effective amount of the fusion protein of claim 1 to the patient, wherein the metabolic disease is diabetes or hepatic steatosis.

16. A fusion protein comprising or consisting of:
a) a first polypeptide, wherein the first polypeptide is glucagon-like peptide-1 (GLP-1) or an analogue thereof;
b) a second polypeptide, wherein the second polypeptide is an IgG4 Fc portion comprising the amino acid sequence of SEQ ID NO: 2 or a variant thereof; and
c) a third polypeptide, wherein the third polypeptide is fibroblast growth factor 21 (FGF21) comprising a variant of the amino acid sequence of SEQ ID NO: 15,
wherein the first polypeptide is linked to the second polypeptide via a first linker and the third polypeptide is linked to the second polypeptide via a second linker; and
wherein the variant of SEQ ID NO: 2 further comprises any one or more mutations selected from E233P and N297A, as compared to a wild-type IgG4 Fc; and
wherein the variant of SEQ ID NO: 15 comprises amino acid mutations at one or more sites of 98 or 171; wherein the amino acid mutation at position 98 is selected from the group consisting of L98D and L98R; and wherein the amino acid mutation at position 171 is selected from the group consisting of P171A and P171G; and
wherein the variant of SEQ ID NO: 15 further comprises one or more mutations at one or more sites selected from the group consisting of 167, 175 and 179; wherein the amino acid mutation at position 167 is selected from the group consisting of S167H and S167C; wherein the amino acid mutation at position 175 is selected from the group consisting of R175L, R175H and R175P; and wherein the amino acid mutation at position 179 is selected from the group consisting of Y179S and Y179F.

17. A pharmaceutical composition comprising the fusion protein of claim 16, and optionally one or more pharmaceutically acceptable adjuvants.

18. A method of treating a metabolic disease in a patient comprising administrating a therapeutically effective amount of the fusion protein of claim 16 to the patient, wherein the metabolic disease is diabetes or hepatic steatosis.

* * * * *